United States Patent [19]
Weiner et al.

[11] Patent Number: 6,039,947
[45] Date of Patent: *Mar. 21, 2000

[54] PEPTIDES DERIVED FROM IMMUNODOMINANT EPITOPES OF MYELIN BASIC PROTEIN

[75] Inventors: Howard L. Weiner, Brookline; David A. Hafler, West Newton, both of Mass.

[73] Assignee: Autoimmune, Inc., Lexington, Mass.

[*] Notice: This patent is subject to a terminal disclaimer.

[21] Appl. No.: 08/297,395

[22] Filed: Aug. 11, 1994

Related U.S. Application Data

[63] Continuation of application No. 08/059,189, May 6, 1993, abandoned, which is a continuation of application No. 07/502,559, Mar. 30, 1990, abandoned, which is a continuation-in-part of application No. PCT/US88/02139, Jun. 24, 1988, abandoned, and a continuation-in-part of application No. 07/065,734, Jun. 24, 1987, abandoned.

[51] Int. Cl.[7] .......................... A61K 39/00; A61K 38/17; C07K 7/08; C07K 14/47
[52] U.S. Cl. .......................... 424/184.1; 514/12; 514/13; 530/300; 530/324; 530/325; 530/326
[58] Field of Search ................ 424/184.1; 530/300, 530/350, 324, 325, 326; 514/12, 13

[56] References Cited

U.S. PATENT DOCUMENTS 4,634,590  1/1987  Cohen et al. .............................. 424/88

FOREIGN PATENT DOCUMENTS

| | | |
|---|---|---|
| 0 304 279 A2 | 2/1989 | European Pat. Off. . |
| 0 271 577 B1 | 10/1995 | European Pat. Off. . |
| WO 80/02501 | 11/1980 | WIPO . |

OTHER PUBLICATIONS

Higgins et al., *J. Immunology*, 140:440–445, 1988.
Eylar, *Adv. Exp. Med. Bio.*, 98:259–281, 1978.
Sriram et al., *Cell Immunol.*, 75:378–382, 1983.
Nagler–Anderson et al., *PNAS*, 83:7443–7446, 1986.
Schoen, *J. Immunol.*, 128:717–719, 1982.
Higgins et al., *Annals Neurology*, abstract No. P154, 1986.
Whitacre et al., *6th Int'l. Cong. Immunol.*, abstract No. 3.62.21, 1986.
Zamvil et al., *Nature*, 324:258–260, 1986.
Fritz et al., *J. Immunol.*, 134:2328–2332, 1985.
Fritz et al., *J. Immunol.*, 130:191–194, 1983.
Pettinelli et al., *J. Immunol.*, 129:1209–1211, 1982.
Whitaker et al., *J. Bio. Chem*, 250:9106–9111, 1975.
Thompson et al., *Clin. Exp. Immunol.*, 64:581–586, 1985.
Lider et al., *J. Immunol.*, 142:748–752, 1989.
Friedman et al., *PNAS*, 91:6688–6692, 1994.
Bitar, dissertation entitled, The Suppressive Effects of Oral Myelin Basic Protein . . . , 1986.
Nagler–Anderson, dissertation entitled, Immunoregulation of an Exp. Model of Autoimmunity, 1986.
Rothbart, 1st Forum in Virology, pp. 518–520, 1986.
Bitar et al., *Cell Immunol.*, 112:364–370, 1988.
Eylar et al., *Neurochem. Research*, 4:249–258, 1979.
Kagnoff, *Oral Tolerance*, pp. 248–269, 1982.
Mowat, *Immunol. Today*, 8:93–98, 1987.
Weiner et al., *Science*, 259:1321–1324, 1993.
Campbell et al, *Arch. Neurol.*, 29:10–15, 1973.
Carnegie et al., *Immunol.*, 19:55–63, 1970.
Fritz et al., *J. Immunol.*, 130:1024–1026, 1983.
Hashim et al., *Arch. Biochem. and Biophy.*, 156:287–297, 1973.
Adorini et al., *Nature* 342:800–2, 1989.
Allegretta, M., et al., *Science*, 247:718–721, 1990.
Avrilionis, K. and Boggs, J.M., *J. Neuroimmunol.* 35:201–10, 1991.
Ben–Nun, A., et al., *J. Immunol.*, 129:303–308, 1982.
Blackman et al., *Science* 248:1335–41, 1990.
Burns, F.R., et al., *J. Exp. Med.*, 169:27–39, 1989.
Buss et al., *Cell* 47:1071–77, 1988.
Cresswell, *Nature* 343:593–94, 1990.
DeFreitas et al., *Proc. Natl. Acad. Sci. USA* 83:2637–41, 1986.
Gaur et al., *Science* 258:1491–4, 1992.
Germain, *Nature* 344:19–22, 1990.
Guillet et al., *Nature* 324:260–62, 1986.
Guillet et al., *Science* 235:865–70, 1987.
Hodes et al., *Science* 246:1041–44, 1989.
Howell, M.D., et al., *Science*, 246:668–670, 1989.
Janeway, *Nature* 341:482–83, 1989.
Kaye et al., *Nature* 341:746–49, 1989.
Lider et al., *Ann. N. Y. Acad. Sci.*, pp. 267–273, 1986.
MacDonald, *Science* 246:982, 1989.
Maritn, R., et al., *J. Immunol.* 145:540–8, 1990.
Martin, R., et al., *J. of Exper. Med.* 173:19–24, 1991.
Martin, R., et al., *J. Immunol.* 148:1359–1366, 1992.
Mokhtarian, F., et al., *Nature*, 309:356–358, 1984.
Nikolic–Zugic et al., *Nature* 344:65–67, 1990.
Ogasawara et al., *Nature* 325:450–52, 1987.
Oksenberg et al., *Nature* 345:344–46, 1990.
Ota, K, et al., *Nature*, 346:183–7, 1990.
Pette, M., et al., *Proc. Natl. Acad. Sci., USA* 87:7968–72, 1990.
Schwartz, *Ann Rev. Immunol.* 3:237–61, 1985.
Su, X., et al., *J. Neuroimmunol.* 34:181–190, 1991.
Vandenbark, A.A., et al., *Nature* 341:541–433, 1989.
Weiner et at., (Abstr) *Neurology* (Suppl. 1) 39:172, 1989.
Wucherpfenning, K.W. et al., *Science* 248:1016–9, 1990.
Zamvil, S. S., et al., *Nature*, 324:258–260, 1986.
Fujimani et al *Science* vol. 230:1043–45, 1985.
Uyemura et al *J Neurobiology* vol. 39:895, 1982.
Hruby et al *J Neurochem* vol. 44:637, 1985.
Jahnke et al *Science* vol. 229:282–284, 1985.
Martenson *J Neurobiology* vol. 40:951, 1983.
Livingstone et al *Ann Rev Immunology* vol. 5 477–501, 1987.
Hurtenbach et al *J Ex Medicine* vol. 177 1499–1504, 1993.
Bishopp *BioWorld Today* vol. 8 No. 92 pp. 1 and 3, May 1997.

*Primary Examiner*—Julie Burke
*Attorney, Agent, or Firm*—Darby & Darby

[57] ABSTRACT

Peptides containing immunodominant epitopes of myelin basic protein that are recognized by groups of T-cells from remitting-relapsing multiple sclerosis patients.

3 Claims, 4 Drawing Sheets

PEPTIDES DERIVED FROM IMMUNODOMINANT EPITOPES OF MYELIN BASIC PROTEIN

This application is a continuation of Ser. No. 08/059,189 filed May 6, 1993, now abandoned which is a continuation of Ser. No. 07/502,559, filed Mar. 30, 1990, now abandoned in turn a continuation-in-part of PCT International Application No. U.S. 88/02139, now abandoned, filed Jun. 24, 1988 and a continuation-in-part of Ser. No. 07/065,734 filed Jun. 24, 1987, now abandoned.

The United States Government has rights to this invention by virtue of funding from Grant Nos. NS 24247, and NS 17182 from the National Institutes of Health.

FIELD OF THE INVENTION

This invention pertains to agents and methods for treating Multiple Sclerosis. More specifically, the invention is directed to therapeutic agents comprising a T-cell receptor and fragments or analogs thereof which are believed to be involved in the pathogenic mechanism of the disease, and to methods of using such agents to suppress disease symptoms.

BACKGROUND OF THE INVENTION

Multiple Sclerosis (MS) is a chronic inflammatory disease of the central nervous system white matter of humans and is believed to be of autoimmune etiology. The disease is characterized by prominent T-cell and macrophage infiltrates, demyelination and neurological dysfunction. Myelin basic protein (MBP) has been extensively studied as a potential autoantigen in the disease because of its role as an inducing agent in the major animal model of MS, experimental allergic encephalomyelitis (EAE), as well as its role in the human disease post viral encephalomyelitis.

A major hypothesis regarding the pathogenesis of MS is that T-cells reactive with myelin basic protein in the white matter of the CNS initiate the inflammatory process. The demonstration that activated T-cells specific for myelin basic protein (MBP) can be isolated from MS patients (Allegretta, M., et al., *Science:* 247: 778, 1990) implicates MBP-reactive T-cells in the pathogenesis of the disease.

Experimental allergic encephalomyelitis (EAE) is the primary animal model for MS. EAE can readily be induced in small mammals by immunization with myelin basic protein (MBP) in an appropriate adjuvant or by passive transfer of CD4+, MBP-reactive T-cells (Alvord Jr, E. C., et al. eds. in *Experimental Allergic Encephalomyelitis: A Useful Model for Multiple Sclerosis*, A. R. Liss, N.Y., 1984; Makhtarian, D. E., et al. *Nature* 309: 356, 1984; Ben-Nun, A. et al. *J. Immunol.* 129:303, 1982). The T-cells that induce EAE in both mice and rats recognize specifically peptides corresponding to species-specific immunodominant regions of MBP presented on antigen-presenting cells by unique Major Histocompatibility Complex (MHC) class II molecules.

T-cell receptors are composed of two distinct chains of protein material. Certain T-cell receptors (TCRs), composed of V-beta (VB) chains and V-alpha (VA) chains, are known to recognize MBP. In SJL/PL mice, encephalitogenic (i.e., disease-inducing when administered to mice) T-cells having these receptors recognize an N-terminal mouse MBP peptide (residues 1–9) presented by an MHC molecule (Zamvil, S. S. et al., *Nature* 324: 258, 1986) encoded by the mouse gene H-2. The majority of T-cell receptors recognizing this peptide presented in connection with the MHC are encoded by the mouse TCR genes VB8.2 and VA2 or VA4. In Lewis rats, TCR gene segments that are homologous with the mouse VB8.2 and TCR VA2 genes have been found in encephalitogenic T-cells which recognize MBP residues 68–88 in the context of the Lewis rat MHC (Burns, F. R., et al., *J. Exp. Med.* 169: 27, 1989). Administration of a VB8.2-specific monoclonal antibody (i.e., an antibody recognizing the product VB8.2 expressed by the corresponding gene) to mice has been shown to be effective in treating murine EAE. Immunization with peptides specifically corresponding to the TCR VB8.2 amino acid sequence ameliorates EAE in the Lewis rat (Vanderbark, A. A., et al., *Nature* 341: 541–544, 1989; Howell, M. D. et al., *Science:* 246, 668; 1989). However, the regions of an autoantigen (such as MBP) that behave as immunodominant regions are species specific. It has not heretofore been determined if common V-gene usage in TCR V-genes exists in humans among T-cells recognizing immunodominant regions of MBP nor have these immunodominant regions been positively identified in MS patients.

The current treatments for MS involve administration of drugs which act in a non-specific fashion to suppress the immune response in the subject. Examples of such drugs are cyclophosphamide, Imuran (azathioprine) and the cyclosporin A. Steroid compounds such as prednisone and methylprednisolone are also employed in many instances. These drugs have limited efficacy against MS. Use of such drugs is limited by toxicity and by the fact that they induce "global" immunosuppression upon prolonged treatment, i.e., they down regulate the normal protective immune response to pathogenic microorganisms thereby increasing the risk of infection. A further drawback is the increased risk that malignancies will develop in patients receiving prolonged global immunosuppression.

Other therapies are being developed for the treatment of autoimmune diseases in general and MS in particular. U.S. patent application Ser. No. 65,794 filed Jun. 24, 1987 (now abandoned) and copending International Patent Application PCT/US88/02139, filed Jun. 24, 1988, disclose that oral or enteral administration of myelin basic protein and of disease inducing and non-inducing fragments and analogs thereof is effective in suppressing acute monophasic EAE and are useful in suppressing MS symptoms when similarly administered.

U.S. patent application Ser. No. 454,806 filed Dec. 20, 1989, now abandoned, discloses the aerosol administration of autoantigens, disease-suppressive fragments of said autoantigens and analogs thereof as an effective treatment for treating T-cell mediated autoimmune diseases such as MS.

A U.S. patent application filed Mar. 3, 1990 entitled "Enhancement of the Down Regulation of Autoimmune Diseases by Oral Administration of Autoantigens" discloses synergists (enhancers) for use with oral administration of autoantigens, disease-suppressive fragments and analogs thereof as effective treatments for T-cell mediated autoimmune diseases.

In furtherance of the efforts and goals expressed in these prior applications, i.e., the design of effective, specific therapeutic treatments for MS, what is needed in the art is to determine if common V-gene usage associated with Major Histocompatibility Complex antigens exists in humans suffering from MS. In other words, there is a need to determine whether encephalitogenic T-cells isolated from human MS victims use restricted TCR VB genes as observed in rodents and whether this function can be exploited to combat disease symptoms. In addition, it is necessary to determine the major immunodominant epitope domain present on human MBP, again with a view towards exploiting all or part of such domain towards therapeutic ends.

It is an object of the present invention to provide agents and methods based upon the human TCR for treating humans suffering from autoimmune diseases having the symptoms of MS.

Another object of the present invention is to provide compositions and pharmaceutical formulations useful for treating humans suffering from autoimmune diseases having the symptoms of MS.

A still further object of the invention is to provide compositions and pharmaceutical formulations useful for administration to humans for the purpose of preventing or attenuating to the manifestation (i.e., clinical symptoms) of autoimmune diseases having the symptoms of MS. Another object of this invention is to provide reagents useful in diagnosis of MS (or of another disease presenting with the same symptoms). (For example TCR-based peptides or peptides based on the immunodominant domain of the human MBP can constitute such diagnostic reagents.)

These and other objects of the present invention will be apparent to those of ordinary skill in the art in light of the present specification, drawings and claims.

SUMMARY OF THE INVENTION

Figure 1:
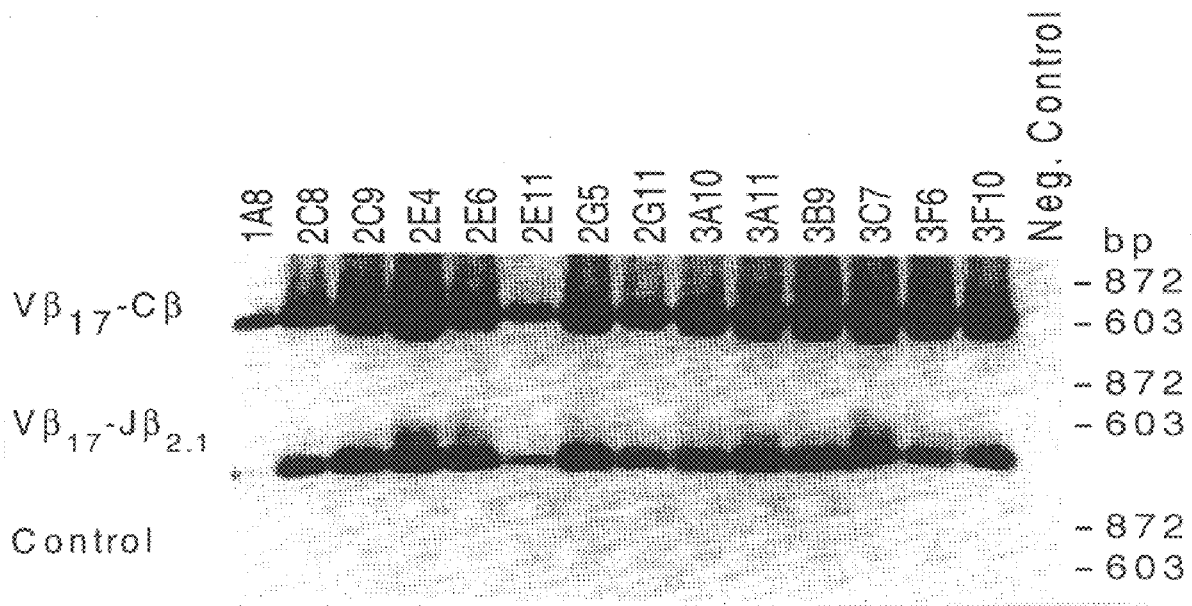
FIG. 1 is an autoradiograph showing PCR amplification of cDNA's from 18 T-cell lines which were generated from five MS patients and which were reactive with MBP residues 84–102, SEQ ID NO: 1.

This invention is directed to therapeutic agents comprising peptides in turn comprising a portion of the T-cell receptor for an antigen involved in immune response of the type manifested in multiple sclerosis. Embodiments of the invention include peptides, vaccines, receptors and entire (attenuated) T-cells.

This invention is also directed to methods using the foregoing agents to suppress immune response against myelin basic protein, and/or to suppress T-cells that recognize an immunodominant epitope of human myelin basic protein.

Additionally, this invention is directed to diagnostic methods and kits for diagnosing multiple sclerosis.

DETAILED DESCRIPTION OF THE INVENTION

All patent applications, patents and literature cited in this specification are hereby incorporated by reference in their entirety.

As used herein, "treatment" is meant to include both prophylactic treatment to prevent an autoimmune disease having the symptoms of MS (or the manifestation of clinical symptoms thereof) as well as the therapeutic treatment, i.e. the suppression or any measurable alleviation of one or more symptoms after the onset of a disease presenting the symptoms of MS.

The term "autoantigen" is defined as any substance normally found within a mammal that, in an abnormal situation, is no longer recognized as part of the mammal itself by the lymphocytes or antibodies of that mammal, and is therefore attacked by the immunoregulatory system as though it were a foreign substance. Examples are MBP and proteolipid peptide (PLP).

"Immunodominant epitope" of an autoantigen (such as MBP) means an antigenic determinant recognized by a majority (although not necessarily an absolute majority) of T-cells of a sensitive species to which such T-cells will mount or help mount an immune response.

"Immunodominant regions" or "immunodominant domains" of an autoantigen (MBP) are defined herein as those regions of the autoantigen containing an immunodominant epitope. The structures (and/or location within the MBP molecule) of immunodominant epitopes (and regions) of MBP vary between species, and are, therefore, species-specific.

"Autoimmune suppressive agents" are defined herein as peptides having the amino acid sequences of (or contained in) VB17 and/or VB12 of the T-cell receptor or analogs thereof as well as other agents (such as attenuated VB17- or VB12-containing T-cells), which when administered to a mammal suffering from a disease having the symptoms of MS will suppress one or more of such symptoms. (The minimum sequence length of the active peptides of the present invention is about 20 amino acids. There is no particular maximum as long as activity is preserved. For example, the entire TCR or even entire T-cells could be used.)

"MHC" or "Major Histocompatibility Complex" is defined as a complex series of mammalian cell surface proteins present on the surface of activated T-cells, macrophages and other immune system cells. The MHC plays a central role in many aspects of immunity both in presenting histocompatibility (or transplantation) antigens and in regulating the immune response against conventional (foreign) antigens. There are two types of MHC protein molecules, class I and class II. The human MHC genes are located on human chromosome 6 and the mouse MHC genes are located in the H-2 genetic locus on mouse chromosome 17.

"Class II MHC molecules" are membrane glycoproteins that form part of the MHC. Class II MHC molecules are found mainly on cells of the immune system including B-cells, macrophages, brain astrocytes, epidermal Langerhan's cells, dendritic cells, thymic epithelium and helper T-cells. Class II MHC molecules are involved in regulating the immune response during tissue graft rejection, stimulation of antibody production, graft-versus-host reactions and in the recognition of "self" (or autologous) antigens, among other phenomena. In the specification below, MHC shall be used interchangeably with "Class II MHC". The MHC genes will be referred to as "MHC genes".

As used herein, "T-cells" or "T-lymphocytes" are defined as immune system cells, derived from stem cells located within hematopoietic (i.e. blood forming) tissues. There are three broad categories of T-cells: Helper, Suppressor and Cytotoxic. T-cells express either the CD4 antigen (and are then called CD4+ T-cells) or the CD8 antigen (in which case they are called CD8+ T-cells) on their cell surface. The expression of CD4 or CD8 antigens by peripheral (circulating) T-cells correlates with the function and specificity of the T-cell. "Helper T-cells" which are CD4+ recognized antigens and Class II MHC molecules and perform helper or regulatory functions. "Cytotoxic" and "Suppressor" T-cells (which are CD8+) recognize antigens and Class I MHC molecules perform suppressor and cytotoxic functions.

"T-cell receptor" or "TCR" is defined herein as the antigen recognition receptor present on the surface of T-cells. TCR is, therefore, the receptor that binds a molecule which the immune system recognizes—and presents—as an antigen (whether the molecule is foreign or autologous, the latter being the case in an autoimmune disease). A majority of T-cells express a TCR composed of a disulfide-bonded heterodimer protein containing one alpha (A) and one beta (B) chain whereas a minority of T-cells express two different chains (gamma and delta). The TCR is composed of an A and a B chain, each of which comprises a variable and a constant region. (Tilinghast, J. P. et al., *Science* 233: 879, 1986; Concannon, P. et al., *Proc. Natl. Acad Sci USA* 83: 6589, 1986, Kimura, N. et al., *J. Exp. Med.* 164: 739, 1986; Toyonaga, B. et al., *Proc Natl. Acad. Sci USA* 82: 8624, 1985.) The variable region in turn comprises a "variable", a "diversity" and "joining" segment. The junction among the variable, diversity and joining segment is postulated to be the site of antigen recognition by T-cells.

T-cells initiate the immune response when antigen presenting cells (APC), such as mononuclear phagocytes (macrophages, monocytes), Langerhan's cells and follicular dendritic cells, initially take up, process (digest) and present antigenic fragments of the polypeptide on their cell surface (in connection with their MHC). CD4+ T-cells recognize antigen molecules exclusively when the protein is processed and peptide fragments thereof are presented by APCs that express Class II MHC molecules.

T-cell recognition of an antigen reflects a trimolecular interaction between the TCR, MHC molecules and peptides processed by APCs via a cleft or pocket in the three-dimensional structure of the Class II MHC molecule. (Bjorkman, P. J., et al., 1987, *Nature,* 329:506 and 329:512).

The present inventors have identified an immunodominant region of MBP resident within a portion of the MBP amino acid sequence (residues 82–104, SEQ ID NO: 1) and two T-cell receptor gene segments which correspond to VB17 and VB12. As shown in Example 2 below, the present inventors have identified human MBP amino acid residues 84–102 as the basis of an immunodominant domain of MBP recognized by a majority of peripheral T-cells isolated from patients suffering from MS. In addition, the present inventors have determined that T-cells reacting with the immunodominant epitope of MBP often also posses the MHC Class II haplotype DR2 gene. The corresponding MHC antigen of such T-cells binds MBP within immunodominant domain composed of residues 82–104 in association with the DR2 phenotype. Since DR2 is most common in patients with MS, these cells can be isolated, identified and used not only to diagnose but also to treat patients with MS (as will be explained below).

In the animal model (EAE) T-cell receptors comprising a portion of the animal VB8.2 sequence have been used to treat the disease and shown to act by eliminating disease-inducing T-cells. In particular, in the animal model, peptides comprising the sequences Thr-Leu-Cys-Ala-Ser-Ser [SEQ ID NO: 3] and Thr-Leu-Cys-Ala-Ser-Arg [SEQ ID NO: 4] which may correspond to exposed (surface) portions of mouse and rat VB8.2 have been determined (in mouse and rat models) to combat the autoimmune disease model by eliminating Helper T-cells.

The present invention can be advantageously used in the design of specific therapeutic agents useful for treating a human suffering from a disease with the symptoms of MS. For example, as shown in Examples 1 and 2 below, peptides comprising sequences of the human VB17 and VB12 can be constructed, e.g., the amino acid sequences Asp Thr Asp Lys Gly Glu Val Tyr Asp Gly (from VB12) [SEQ ID NO: 5] and Phe Gln Lys Gly Asp Ile Ala Glu Gly Tyr (from VB17) [SEQ ID NO: 6] and used for therapeutic purposes. Other active peptides are those comprising the sequence JYYSQIVND-FQKGDIAEGYS [SEQ ID NO: 7]. Additional active peptides can be designed based on the amino acid sequences of the entire human VB17 and VB12 or fragments or analogs thereof.

The amino acid sequence for human VB12 [SEQ NO ID: 8] (and one of the possible nucleic acids encoding it SEQ ID NO: 9) is set forth below:

LeuArgCysHisGlnThrGluAsn-
  HisArgTyrMetTyrArgGlnAspProGlyHisGly CTGAGAT-
  GTCACCAGACTGAGAACCACCGCTATAT-
  GTACCGACAAGACCCGGGGCATGGG
LeuArgLeuIleHisTyrSerTyrGly-
  ValLysAspThrAspLysGlyGluValSerAsp CTGAGGCT-
  GATCCATTACTCATATGGTGTTAAA-
  GATACTGACAAAGGAGAAGTCTCAGAT
GlyTrySerValSerArgSerLysThr-
  GluAspPheLeuLeuThrLeuGluSerAlaThr GGCTATAGT-
  GTCTCTAGATCAAAGACAGAGGATTTC-
  CTCCTCACTCTGGAGTCCGCTACC
SerSerGlnThrSerValTyrPheCysAlaAsn AGCTCCCAGA-
  CATCTGTGTACTTCTGTGCCAAT

The amino acid sequence for human VB17 [SEQ ID NO: 10] (and one of the possible nucleic acids encoding it [SEQ ID NO: 11]) is set forth below:

AspGlyGlyIleThrGlnSerProLy-
  sTyrLeuPheArgLysGluGlyGlnAsnValThr GATGGTG-
  GAATCACTCAGTCCCCAAAGTACCTGT-
  TCAGAAAGGAAGGACAGAATGTGACC
LeuSerCysGluGlnAsnLeuAsn-
  HisAspAlaMetTyrTrpTyrArgGlnAspProGly CTGAGT-
  TGTGAACAGAATTTGAACCACGATGC-
  CATGTACTGGTACCGACAGGACCCAGGG
GlnGlyLeuArgLeuIleTyrTyrSer-
  GlnIleValAsnAspPheGlnLysGlyAspIle CAAGGGCT-
  GAGATTGATCTACTACTCACAGATAG-
  TAAATGACTTTCAGAAAGGAGATATA
AlaGluGlyTrySerValSerArgGlu-
  LysLysGluSerPheProLeuThrValThrSer GCTGAAGGG-
  TACAGCGTCTCTGGGAGAAGAAG-
  GAATCCTTTCCTCTCACTGTGACATCG
AlaGlnLysAsnProThrAlaPheTyrLeuCysAlaSerSer
  GCCCAAAAGAACCCGACAGCTTTC-
  TATCTCTGTGCCAGTAGT (Notwithstanding the identity between mouse peptide TKCASS and the C-terminal human VB17, peptides encompassing this amino acid sequence are not expected to be active in humans because this sequence is a fairly common terminal sequence in human VB chains and hence would not have as specialized a function as required for activity in suppressing MS symptoms.)

Without wishing to be bound by theory, it is believed that administration of VB17- or VB12-based peptides especially those incorporating the fragments previously identified above or active analogs thereof to patients suffering from MS will block the TCR or kill T-cells that express TCR and thereby block the induction or activation of Helper T-cells involved in mounting an immune response against the myelin sheath of the central nervous system (CNS) in patients suffering from MS. The mechanism of this may involve the production of anti-VB (12 or 17) antibodies, i.e., native antibodies that will recognize VB12 and/or VB17 and therefore bind to TCR. Whatever the mechanism of action, these VB12- and VB17-based peptides are fully expected to be effective in attenuating or eliminating symptoms of MS or of a disease presenting with the same symptoms and are, therefore, expected to be useful therapeutic agents or adjuncts to MS therapy. (For example, parenteral administration of such peptides may supplement or be supplemented by oral and/or aerosol administration of MBP or fragments or analogs of MBP as disclosed for example in U.S. patent appls. Ser. No 487,732 filed Mar. 2, 1990 and entitled "Enhancemen of the Down-Regulation of Autoimmune Diseases by Oral Administration of Autoantigens", and Ser. No. 454,806 filed Dec. 20, 1989.

In addition, healthy individuals susceptible to MS (i.e. individuals having the DR2 haplotype) and expressing VB17 or VB12 TCR on their T-cells, and therefore having T-cells that proliferate (or that could be induced to proliferate) in response to the presentation of the immunodominant region of human MBP may also benefit from prophylactic administration of the peptide. In Example 2 below, VB17 was significantly less frequently present (only in approximately 9.4% of the cell population collected) on T-cells isolated from a normal individual than was present on the T-cell lines reactive with human MBP amino acid residues 84–102 (53.9%) isolated from five MS patients. In addition, VB12 was identified on 35% (7/20) of T-cell lines reactive with MBP amino acid residues 84–102 isolated from 4 MS patients (as opposed to 15% of T-cells from normal controls). These results show that the VB17 and VB12 TCR peptides are selectively involved in the recognition of the immunodominant (possibly encephalitogenic) human MBP region. Therefore, it is anticipated that these peptides or fragments or analogs thereof will provide safe, effective therapeutic agents for treatment or prophylaxis of humans against MS symptoms.

Peptides based on the sequences of VB17 or VB12 for use in the present invention can be synthesized using well-known solid phase methods (Merrifield, R. B. *Fed. Proc. Am. Soc. Ex. Biol.* 21: 412, 1962 and *J. Am. Chem. Soc.* 85: 2149, 1963; Mitchel, A. R. et al, *J. Am. Chem. Soc.* 98: 7357, 1976; Tam, J. et al., *J. Am. Chem. Soc.* 105: 6442, 1983). Alternatively, such peptides can be synthesized by recombinant DNA techniques, as is now well-known in the art (Maniatis et al. *Molecular Cloning: A Laboratory Manual*, Cold Spring Harbor Laboratories, N.Y., 1982, see pp. 51–54 and pp. 412–30). For example, these peptides can be obtained as the expression products after incorporation of DNA sequences encoding VB12 or VB17 (or fragments or analogs thereof) into expression vectors and introduction of such vectors into suitable eukaryotic or prokaryotic hosts that will express the desired peptides individually or as part of fusion peptides or proteins.

Peptide analogs can be designed using the known amino acid sequences encoded by the VB17 or VB12 genes as disclosed below, using the synthetic or recombinant techniques described above and the methods of, e.g., Eyler, E. H., in *Advances in Experimental Medicine and Biology* 98: 259–281, 1978. For example, a peptide having a sequence based upon the amino acid sequence of VB12 or VB17 can be chemically synthesized using the above-described techniques. The peptide can be tested for disease-suppressive activity when administered to a mammal using, for example, the experimental protocol of Howell, M. D. et al., *Science*, 246: 668, 1989 or Vanderbark, A. A. et al., *Nahire,* 341: 541, 1989.

In addition, T-cells which are VB17+ or VB12+ can be isolated from patients suffering from MS and identified using the techniques described in Examples 1 and 2 below. These isolated VB17+ or VB12+ T-cells can be expanded, cloned, attenuated (as described by Lider, O., et al., 1986, *Ann. N.Y. Acad. Sci.*, pp.267–273 and by Weiner, H. L., et al. (Abstr.) *Neurology* (Suppl. 1) 69:172, 1989) and used as specific therapeutic agents/immunogens to treat patients suffering from MS (preferably the same patents from whom the T-cells were originally isolated). T-cell attenuation can be effected, for example, by exposing the T-cells to 0.1% glutaraldehyde for 15 min. at room temperature. T-cell clones grown to 50 million cells in vitro and attenuated (as described) can be stored in phosphate buffer saline (PBS). A dosage of 50 million thus treated VB17+ and/or VB12+ cells can be injected e.g. subcutaneously.

The present invention also provides a kit containing isolated nucleic acids (RNA or DNA) having the sequence 5'GATACTGACAAAGGAGAAGTCTCAGATGGC3' [SEQ ID NO: 12] and/or 5'TTTCAGAAAGGAGATAT-AGCTGAAGGGTAC3' [SEQ ID NO: 13] or analogs thereof encoding all or portion of VB12 and VB17, respectively, and sequences which hybridize with these sequences under stringent hybridization conditions (such as those described below in Example 1) can be used to diagnose MS and susceptibility to MS, and to monitor disease progression. T-cells can be isolated from patients, cloned, expanded and probed for the presence of VB12 and/or VB17 using for example the techniques described below in Examples 1 and 2, or other assay techniques well-known in the art.

The present invention also provides pharmaceutical formulations and dosage forms for use in treating mammals suffering from diseases having the symptoms of MS. In general such dosage forms contain one or more autoimmune-disease suppressive agents comprising peptides in turn comprising (i) the sequence of human VB12 and/or VB17 and (ii) disease suppressive fragments and analogs thereof, in an amount effective to treat or prevent one or more clinical symptoms of MS. Any clinically significant attenuation of one or more symptoms of MS that has been treated pursuant to the methods of the present invention is considered to be a treatment of such disease within the scope of the invention.

The autoimmune disease suppressive agents of the present invention may also encompass additional amino acids in sequences leading or following the VB17 or VB12- based sequences as long as these additional sequences do not defeat the disease-suppressive function of such agents. Testing of such constructs for disease-suppressive activity can be easily done using, for example, one or more of the methods described below.

It will be appreciated that the unit content of active ingredient or ingredients contained in an individual dose of each dosage form need not in itself constitute an effective amount for treating MS since the necessary effective amount can be reached by administration of a plurality of dosage units.

The pharmaceutical formulations of the present invention may include, as optional ingredients, pharmaceutically acceptable vehicles, carriers, diluents, solubilizing or emulsifying agents, and salts of the type that are well-known in the art. Nonlimiting examples of such substances include 0.5N saline in distilled water for parenteral use, lyophilized T-cell receptor or peptide diluted in lactose for oral use, adjuvants such as alum or tenanus toxoid or MAPS (disclosed in J. R. Tam et al., *J. Exp. Med.* 171:299–306, 1990; and Tam, J. R. Proc. Natl. Acad. Sci. 85:5409, 1988) for vaccination with peptides although larger peptide constructs such as whole TCR may not need an adjuvant.

The preferred route of administration of the suppressive agents of the present invention is in a parenteral form including intraperitoneal, intravenous, intradermal and most preferably subcutaneous administration routes. Preferred pharmaceutical formulations may comprise for example, formulations containing between about 0.3 mg and about 200 mg of one or more of the agents of the present invention specific for MS.

In general, the VB12- or VB17-based peptide or analog is introduced to a mammal in an amount preferably ranging between about 0.3 mg per kg body weight of said mammal and about 200 mg per kg body weight of said mammal preferably administered once every 3 months and may be administered in a single dosage form or multiple dosage forms. The exact amount and frequency of administration to a patient is subject to optimization and may vary depending on the stage, frequency of manifestation and severity of the patient's disease and the physical condition of the patient, as is well known in the art. Such optimization is preferably effected on a case-by-case basis. Customized therapy is common for MS patients and thus, optimization of dosage represents ordinary experimentation. One preferred method of optimizing dosage is as follows: T-cells are obtained from a patient and cultured, the culture is expanded and T-cell DNA is collected.

The techniques described below in Examples 1–3 can be used to monitor the effectiveness of the methods of the present invention and optimize the amount and frequency of administration of the disease suppressive agents of the present invention.

T-cells can be isolated from a patient's peripheral blood, amplified and cloned as described in Examples 1–3 below (before and/or after treatment according to the present invention) and probed for the presence of VB12+ and/or VB17+ T-cells using PCR amplification with the specific VB primers shown in Table 2 below. A reduction or elimination of VB12+ or VB17+ T-cells after treatment with VB12 and/or VB17 based peptides of the present invention will provide an objective measurement of a patient's disease status. Therefore, the exact amount and frequency of administration of the agents of the present invention can be optimized.

Alternatively, antibodies (either polyclonal or monclonal) can be obtained directed against the VB12 and/or VB17 polypeptides of the present invention (using conventional techniques well known and used in the art) to assay for the presence of VB12+ and/or VB17+ T-cells in a patient's peripheral blood before and/or after treatment according to the present invention.

When isolated, attenuated VB17+ or VB12+ T-cells are administered to a patient, either prophylactically or for the treatment of active disease, the effective amounts can be easily determined, for example as follows: An amount of such T-cells, e.g., 50 million, is administered to a patient. Two weeks later, T-cells are collected from the patient and probed for the presence of T-cells expressing VB12 or VB17. If such T-cells have been significantly reduced, the dosage is effective. The preferred route of administration for this embodiment of the present invention is parenteral, and most preferably subcutaneous.

As shown in the Examples below, reactivity with MBP residues 84–102 is associated with the DR2 gene. The TCR VB gene used in three healthy DR2+ individuals was examined (controls 1–3, Table 3). 5/5 cell lines from a normal DR2+ subject were VB17+, whereas one of the two cell lines from another normal DR2+ was VB12+. These data show that VB17 and VB12 are TCR recognition elements for this immunodominant region in MS patients and in healthy DR2+ individuals.

The present invention is described further below in specific examples which are intended to illustrate the present invention without limiting its scope.

EXAMPLE 1

Techniques

MBP was extracted from human brain tissue and purified on a CM-52 column using the highest molecular weight peak (18 kD) as described (Chou, F. C.-H. et al *J. Biol. Chem.* 251: 2671, 1976). MBP peptides were synthesized using a solid phase method and were obtained from a commercial laboratory (Biosearch Lab Inc., San Raphael, Calif.) and were purified by high pressure liquid chromatography. The MBP peptide fragments used are set forth below in Table 1.

TABLE 1

| MBP Amino Acid Residues | Sequence | MBP Amino Acid Residues | Sequence |
|---|---|---|---|
| 1–20: | ASQKRPSQRHGSKYLATAST | 11–30: | GSKYLATASTMDHARHGFLP |
| 21–40: | MDHARHGFLPRHRDTGILDS | 31–50: | RHRDTGILDSIGRFFGGDRG |
| 41–60: | IGRFFGGDRGAPKRGSGKDS | 51–70: | APKRGSGKDSHHPARTAHYG |
| 61–82: | HHPARTAHYGSLPQKSHGRT | 71–92: | SLPQKSHGRTQDENPVVHFF |
| 84–102: | DENPVVHFFKNIVTPRTPP | 93–112: | KNIVTPRTPPPSQGKGRGLS |
| 113–132: | LSRFSWGAEGQRPGFGYGGR | 124–142: | RPGFGYGGRASDYKSAHKG |
| 143–168: | FKGVDAQGTLSKIFKLGGRD | | |

Amino acid residues 1–20 are identified as [SEQ ID NO: 14], amino acid residues 11–30 are identified as [SEQ ID NO: 15], amino acid residues 21–40 are identified as [SEQ ID NO: 16], amino acid residues 31–50 are identified as [SEQ ID NO: 17], amino acid residues 41–60 are identified as [SEQ ID NO: 18], amino acid residues 51–70 are identified as [SEQ ID NO: 19], amino acid residues 61–82 are identified as [SEQ ID NO: 20], amino acid residues 71–92 are identified as [SEQ ID NO: 21], amino acid residues 84–102 are identified as [SEQ ID NO: 1], amino acid residues 93–112 are identified as [SEQ ID NO: 22], amino acid residues 113–132 are identified as [SEQ ID NO: 23], amino acid residues 124–142 are identified as [SEQ ID NO: 24], and amino acid residues 143–168 are identified as [SEQ ID NO: 25].

T-cell receptor TCR VB gene usage was determined by polymerase chain reaction (PCR) amplification using a panel of TCR VB primers followed by Southern blotting. T-cell lines were established from peripheral blood mononuclear cells by two rounds of stimulation with MBP followed by stimulation with an immunodominant human MBP peptide (amino acid residues 84–102), immunodominance of which had been determined by proliferation assays (as described in Example 2) using the Table 1 panel of 13 overlapping MBP peptides. Following a third round of stimulation with their specific MBP peptide, RNA was extracted from MBP-reactive T-cell culture pellets (20,000–50,000 cells) by extraction with guanidium-isothiocyanate/phenol-chloroform and isopropanol precipitation in the presence of carrier tRNA. Single-stranded cDNAs were synthesized using oligo-dT and AMV-reverse transcriptase (both available commercially from Bethesda Research Laboratories, Gaithersburg, Md.). PCR (polymerase chain reaction as disclosed in U.S. Pat. No. 4,800,159 issued Jan. 24, 1989; U.S. Pat. No. 4,683195 issued Jul. 28, 1987; and U.S. Pat. No. 4,683,202 issued Jul. 28, 1987) amplification was performed using a panel of 19 oligonucleotides (specific for published TCR VB families—VB 1–20, Table 2) corresponding to the CDR2 region of the TCR B-chain and a CB (constant region of B chain) primer (Table 2) (as disclosed in Tilinghast, J. P. et al., *Science* 233: 879, 1986; Concannon, P. et al., *Proc. Natl. Acad. Sci.* 83: 6598, 1986; Kimura, N. et al., *J. Exp. Med.* 164: 739, 1986; Toyonaga, B. et al. *Proc. Natl. Acad. Sci.* 82: 8624, 1985; Kimura, N. et al., *Eur. J. Immunol.* 17: 375, 1987). Amplifications were done for thirty cycles (94° C. 1 min., 55° C. 2 min., 72° C. 3 min.) using 1 microgram of each primer in 50 microliter reactions. Amplified products were separated in 1% agarose gels, transferred to nitrocellulose and Southern blots were hybridized with an internal oligonucleotide TCR-CB probe (Table 2). Probes were endlabeled with $^{32}$P gamma-ATP and T4 polynucleotide kinase (Bethesda Research Labs.) to a specific activity of $10^8$ cpm/ug and hybridized in 6×SSC/5× Den-hardt's/0.05% pyrophosphate/100 ug/ml denatured DNA/0.5% SDS for 18 hours at 37° C. Blots were washed at a final stringency of 6×SSC/70° C. and autoradiographed for 2–18 hours. T-cell lines that were positive for more than two VB segments were considered not to be derived from a single MBP reactive T-cell and therefore excluded from analysis.

For sequencing, amplifications of cDNAs were performed with a VB17 primer (Table 2) specific for the leader segment containing an internal Pst I restriction site. Amplified DNA was treated with proteinase K, phenol/chloroform extracted, ethanol precipitated and digested with restriction endonucleases Bgl II and Pst I (available commercially, e.g., from Bethesda Research Labs., supra). Gel-purified DNA was ligated into M13 mp18 and single-stranded DNA was sequenced by the dideoxy-method (Sanger, F., et al., 1977, *Proc. Nat'l. Acad. Sci.*, 74:5463). Negative controls were included during the procedure to test for possible contamination of RNA samples or reagents used for cDNA synthesis and amplification. The VB, CB and JB2.1 primer sequences used are set forth below in Table 2.

Amplified and non-amplified samples were handled separately, reagents were aliquoted and tested for the presence of amplified material and negative controls were included for different experimental steps (RNA isolation, cDNA synthesis, PCR amplification).

TABLE 2

| | | |
|---|---|---|
| VB1 | 5'AAGAGAGAGCAAAAGGAAACATTCTTGAAC3' | [SEQ ID NO:26] |
| VB2 | 5'GCTCCAAGGCCACATACGAGCAAGGCGTCG3' | [SEQ ID NO:27] |
| VB3 | 5'AAAATGAAAGAAAAAGGAGATATTCCTGAG3' | [SEQ ID NO:28] |
| VB4 | 5'CTGAGGCCACATATGAGAGTGGATTTGTCA3' | [SEQ ID NO:29] |
| VB5 | 5'CAGAGAAACAAAGGAAACTTCCCTGGTCGA3' | [SEQ ID NO:30] |
| VB6 | 5'GGGTGCGGCAGATGACTCAGGGCTGCCCAA3' | [SEQ ID NO:31] |
| VB7 | 5'ATAAATGAAAGTGTGCCAAGTCGCTTCTCA3' | [SEQ ID NO:32] |
| VB8 | 5'AACGTTCCGATAGATGATTCAGGGATGCCC3' | [SEQ ID NO:33] |
| VB9 | 5'CATTATAAATGAAACAGTTCCAAATCGCTT3' | [SEQ ID NO:34] |
| VB10 | 5'CTTATTCAGAAAGCAGAAATAATCAATGAG3' | [SEQ ID NO:35] |
| VB11 | 5'TCCACAGAGAAGGGAGATCTTTCCTCTGAG3' | [SEQ ID NO:36] |
| VB12 | 5'GATACTGACAAAGGAGAAGTCTCAGATGGC3' | [SEQ ID NO:37] |
| VB14 | 5'GTGACTGATAAGGGAGATGTTCCTGAAGGG3' | [SEQ ID NO:38] |
| VB15 | 5'GATATAAACAAAGGAGAGATCTCTGATGGA3' | [SEQ ID NO:39] |
| VB16 | 5'CATGATAATCTTTATCGACGTGTTATGGGA3' | [SEQ ID NO:40] |
| VB17 | 5'TTTCAGAAAGGAGATATAGCTGAAGGGTAC3' | [SEQ ID NO:41] |
| VB18 | 5'GATGAGTCAGGAATGCCAAAGGAACGATTT3' | [SEQ ID NO:42] |

TABLE 2-continued

| | |
|---|---|
| VB19 | 5'CAAGAAACGGAGATGCACAAGAAGCGATTC3' [SEQ ID NO:43] |
| VB20 | 5'ACCGACAGGCTGCAGGCAGGGGCCTCCAGC3' [SEQ ID NO:44] |
| CB | 5'GGCAGACAGGACCCTTGCTGGTAGGACAC3' [SEQ ID NO:45] |
| C-probe | 5'TTCTGATGGCTCAAACACAGCGACCTCGGG3' [SEQ ID NO:46] |
| VB17-Leader | 5'AGCAACCAGGTGCTCTGCAGTGTGGTCCTT3' [SEQ ID NO:47] |
| JB2.1 | 5'CCCTGGCCCGAAGAACTGCTCATTGTAGGA3' [SEQ ID NO:48] |

EXAMPLE 2

Identification of VB Gene Usage in T-Cells Isolated from MS Patients

Two series of experiments were performed to test the validity of the above-described approach. First, it was demonstrated that all Table 2 primers except VB20 were able to amplify cDNA from peripheral blood T-cells (FIG. 1). Secondly, the specificity of PCR amplifications was examined by analysis of VB gene usage in 69 independent T-cell clones previously established by single cell cloning with mitogen (such as phytohemagglutin,—"PHA"—and interleukin-2). Due to the high cloning efficiencies obtained, these clones provided a representative analysis of VB gene usage among peripheral blood T-cells. TCR VB gene usage could be determined for 65/69 (94.2%) of these T-cell clones indicating that a large proportion of the TCR VB repertoire was covered by the VB primers. While 58 of these clones (84%) were positive for a single VB, 7 clones (10.1%) were double-positive, possibly due to the presence of two rearranged and expressed TCR VB genes.

The TCR VB gene usage was then analyzed in sixty-five MBP-specific T-cell lines established from five patients with clinically-defined relapsing-remitting MS. Representative Southern blots from MBP reactive T-cell lines are shown in FIG. 1 and VB genes usage for all cell lines analyzed are set forth in Table 3 below.

TABLE 3

| CELL LINE | TCR VB | CELL LINE | TCR VB | CELL LINE | TCR VB |
|---|---|---|---|---|---|
| MBP PEPTIDE 84-102 REACTIVE T-CELL LINES MULTIPLE SCLEROSIS | | | | | |
| Patient 1 (DR2. DR7) | | Hy.2C12 | VB17,VB1 | Cy.2C2 | VB12 |
| HY.1B12 | VB17 | Hy.2E2 | VB17,VB1 | Cy.3F6 | VB12 |
| Hy.1G9 | VB17 | Hy.2E11 | VB17,VB2 | Cy.4C1 | VB12 |
| Hy.1H7 | VB17 | Hy.3A11 | VB17,VB2 | Patient 3 (DR2,DR4) | |
| Hy.2C9 | VB17 | Hy.2C8 | VB17,VB11 | Ns.2A5 | VB1 |
| Hy.2E4 | VB17 | Hy.3B7 | VB4 | Ns.2C10 | VB3,VB14 |
| Hy.2E6 | VB17 | Hy.3C3 | VB4 | Ns.2D11 | VB5,VB7 |
| Hy.2F10 | VB17 | Hy.3C6 | VB4 | Ns.1G11 | VB12,VB17 |
| Hy.2G5 | VB17 | Hy.2F11 | VB7 | Ns.2E2 | VB12,VB17 |
| Hy.2G11 | VB17 | Hy.3B12 | VB7 | Patient 4 (DR2,DR7) | |
| Hy.3A8 | VB17 | Hy.1H3 | VB14 | Fn.1M7 | VB4 |
| Hy.3A10 | VB17 | Hy.2B2 | VB14 | Fn.3E17 | VB3,VB5 |
| Hy.3B9 | VB17 | Hy.2H9 | VB14 | Fn.1E6 | VB6,VB8 |
| Hy.3C7 | VB17 | | | Fn.1G6 | VB17 |
| Hy.3G10 | VB17 | Patient 2 (DR2,DRw11) | | Patient 5 (DR2,DR4) | |
| Hy.3F6 | VB17 | Cy.2H11 | VB1,VB7 | Tw.1B11 | VB12 |
| Hy.3F7 | VB17 | Cy.3D2 | VB1,VB7 | Tw.2F3 | VB12,VB17 |
| Hy.3F10 | VB17 | Cy.2C6 | VB2 | Tw.E10 | VB17 |
| Hy.1A8 | VB17 | Cy.2G5 | VB17 | Tw.2E2 | VB14 |
| CONTROLS | | | | | |
| Control 1 (DR2,DR4) | | Control 2 (DR2) | | Control 4 (DR7,DRw11) | |
| Rt.1A9 | VB17 | Hr.1B7 | VB12 | An.3E1 | VB1,VB8 |
| Rt.3C1 | VB17 | Hr.1C9 | VB5 | An.3H3 | VB8 |
| Rt.3G11 | VB17 | Control 3 (DR2) | | An.3C12 | VB2 |
| Rt.3A3 | VB17,VB14 | Md.2A4 | VB6,VB8 | Control 5 (DR1,DR9) | |
| Rt.3F1 | VB17,VB14 | Md.2F1 | VB8,VB18 | Cr.1B12 | VB17,VB12 |

TABLE 3-continued

| CELL LINE | TCR V8 | CELL LINE | TCR V8 |
|---|---|---|---|
| MBP PEPTIDE 143-168 REACTIVE T-CELL LINES MULTIPLE SCLEROSIS | | | |
| Patient 2 (DR2,DRw11) | | Patient 3 (DR2,DR4) | |
| Cy.1E6 | VB14 | Ns.2D6 | VB3 |
| Cy.2B12 | VB14 | Patient 4 (DR2,DR7) | |
| Cy.2E2 | VB14 | Fn.1H5 | VB4 |
| Cy.3G10 | VB14 | Fn.2A10 | VB4 |
| Cy.3H10 | VB14,VB8 | Fn.2A5 | VB2 |
| Cy.4C10 | VB14,VB17 | Patient 5 (DR3,DR4) | |
| Cy.1C12 | VB12 | Tw.2C9 | VB12 |
| Cy.1E9 | VB7 | | |
| Cy.3F9 | VB1 | | |
| CONTROLS | | | |
| Control 3 (DR2) | | Control 6 (DR1,DR7) | |
| Hr.2E10 | VB3,VB5 | Bn.2G1 | VB12 |
| Hr.3E9 | VB7 | Bn.3D6 | VB12 |
| | | Bn.3C10 | VB5,VB8 |

Fifty-one of these lines reacted with MBP residues 84–102, while fourteen T-cell lines were specific for MBP residues 143–168. Thirty-one MBP T-cell lines reactive to MBP amino acid residues 84–102 were analyzed from MS patient Hy (patient 1, Table 3). Twenty-three of these T-cell lines (74%) were found to use the VB17 gene segment, while eight other cell lines were restricted by either VB2, VB7 or VB14 gene segments. These results indicate that VB17 is the major recognition element in T-cell lines from this MS patient reactive with MBP residues 84–102. VB17 usage was also found among 6/20 T-cell lines examined from four other patients (patients 2–5, Table 3). The second TCR VB that was used by T-cell lines among these four patients was VB12 which was found in 7/20 T-cell lines reactive with MBP residues 84–102 (Table 3, FIG. 1). This VB happens to be homologous to the mouse VB8.2 which is the predominant TCR used among encephalitogenic T-cells in mice and rats (Burns, F. R. et al., *J. Exp. Med.* 169: 27, 1989).

MS patient Cy expressed both the DR2 and DRw11 antigens and thus had T-cells that recognized either the immunodominant MBP region (84–102 residues) or the MBP 143–168 residues. This provided the opportunity to compare TCR VB usage among T-cells reacting to different MBP determinants (FIG. 1). Of seven lines proliferating to MBP residues 84–102, three expressed VB12 and one expressed VB17 (Table 3). In contrast, 6/9 T-cell lines recognizing the MBP residues 143–168 used VB14 and only one line each used the TCR VB12 and VB17 TCR genes (Table 3). Southern blot analysis of five T-cell lines reactive with MBP residues 84–102 (VB12: Cy.2C2, Cy.3F6) or MBP residues 143–168 (VB14:Cy.1E6, Cy.2B12, Cy.2E2) are shown in FIG. 1.

While VB12/VB13 is relatively common among normal peripheral blood T-cells (approximately 18%), VB17 is significantly less frequent (approximately 3%), as assessed by quantitative PCR. In contrast, VB17 was found in 34/63 (53.9%) of T-cell lines reactive with MBP residues 84–102, while it was only present in 3/32 (9.4%) of TCR VB genes in random mitogen derived T-cell clones obtained by single-cell cloning from a normal individual (Moretta, A. et al., *J. Epp. Med.* 157: 743, 1983; Hafler, D. A., et al., *J. Exp. Med.* 167: 1313, 1988). These data indicate that the VB17 TCR is selectively involved in the recognition of the immunodominant MBP 84–102 region.

In order to show that the TCR gene segment identified by PCR was the VB encoding gene used to recognize the MBP peptide, two VB17 positive T-cell lines (Hy.2H9 and Hy.2G5) were cloned by limiting dilution (Moretta, supra.). 11/11 individual clones established from these two cell lines, which were reactive with both MBP and MBP residues 84–102, were VB17+. Three of these clones were further analyzed using the complete panel of VB primers and were all found to be negative for the other VB segments.

Figure 2:
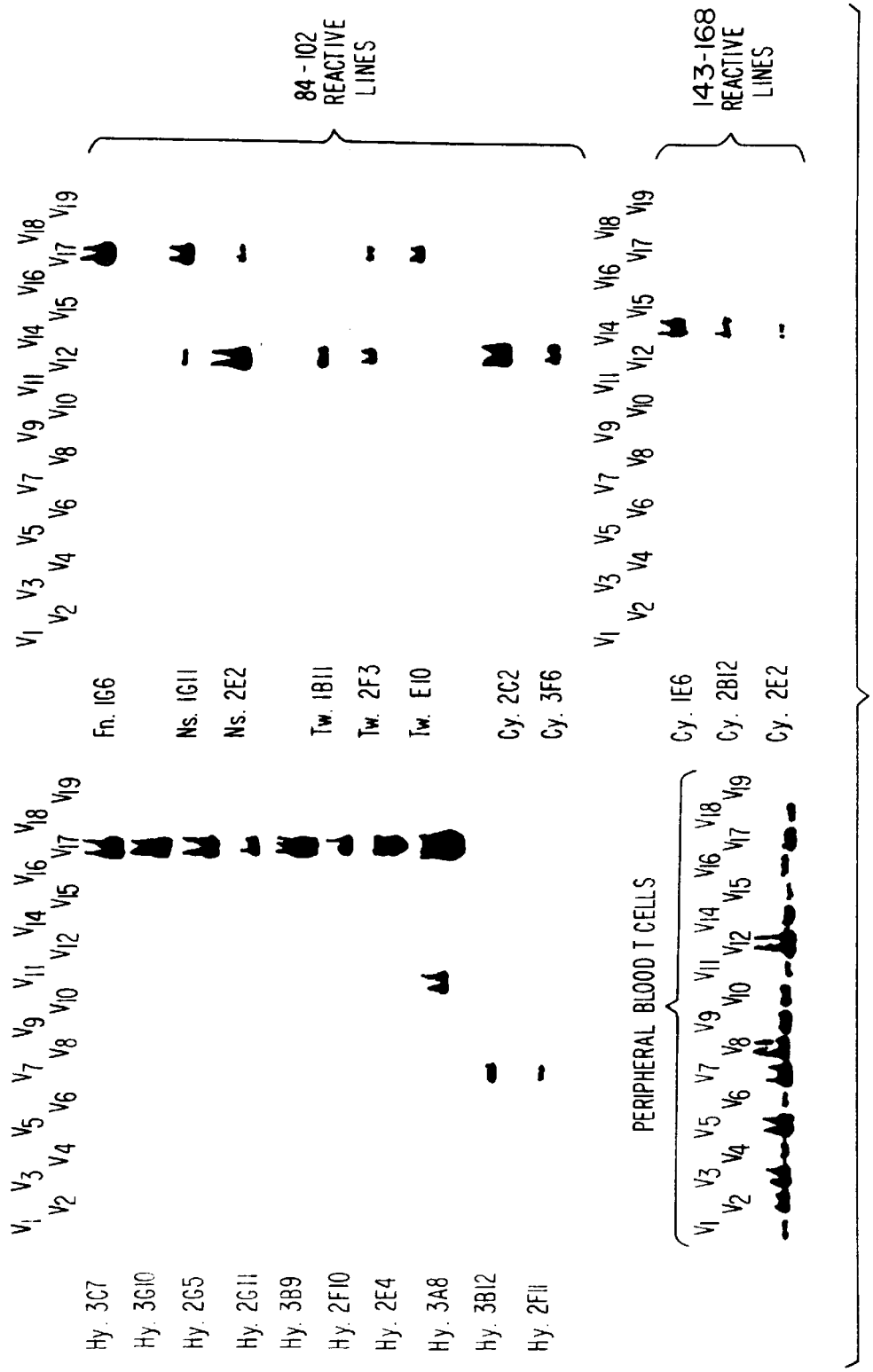
FIG. 2 is an autoradiograph of a Southern blot analysis of TCR VB and JB gene usage for MBP-reactive T-cell lines generated from peripheral blood of an MS patient.

The VB sequences of four T-cell lines from patient Hy were found to be 100% homologous to the published VB17 sequence (as disclosed in Kimura, N., et al., *Eur. J. Immunol.* 17: 375, 1987). This sequence analysis confirms that specific VB segments were indeed amplified using this approach. Analysis of the VDJ (diversity-junctional) sequence indicated that all four of these T-cells used the same junctional JB2.1 segment and that ¾ of them had the same VDJ sequence (Table 2). To determine how frequently the JB2.1 gene segment was used by VB17+ T-cells, the DNAs from 20 cell lines from MS patient Hy were amplified using the VB17 primer combination with a CB primer or a JB2.1 primer (FIG. 2). All of these lines were found to be positive for VB17 as well as JB2.1 gene segments, while the negative controls (RNA extracted from all cell lines and not converted to cDNA, and reagents used for cDNA synthesis and amplification) were negative by PCR and Southern blotting. These data show a strong selection for the VB17–JB2.1 sequence elements in with MBP residues 84–102 reactive T-cell lines derived from patient Hy.

Two other T-cell lines using the VB17 TCR identified by PCR analysis and recognizing MBP residues 84–102 from MS patients Fn and Ns were sequenced and compared to sequences of TCR VB from MS patient Hy (Table 3). While the VB17 gene segment sequence was identical among T-cells reactive MBP residues 84–102 from the three patients, different JB sequence elements were found. Three results show a shared VB gene usage in T-cells recognizing an immunodominant MBP peptide between different individuals. In contrast, shared JB gene segment usage was found among T-cells derived from the same individual but not between different individuals.

Four of the five patients studied were positive for the disease-associated DR2 allele, while patient Tw was HLA-DR3, DR4. Nevertheless, three VB12/VB17 restricted cell lines were present among four lines analyzed from this MS patient (Table 3), indicating that shared MHC Class II antigens may not be mandatory for shared TCR VB gene usage with respect to recognition of MBP peptide 84–102.

EXAMPLE 3

Identification of the Major Immunodominant Region of Human MBP

A rapid T-cell cloning technique was used to examine whether there were immunodominant epitopes on human MBP reactive with Class II MHC phenotypes and the frequency of such reactivity. A total of 15,824 short term T-cell lines were generated from 51 subjects by culturing peripheral blood mononuclear cells (PMN) with purified MBP (obtained as in Example 1 above) followed 3 days later, and then every 3–4 days, by the addition of Interleukin-2 (IL-2) and Interleukin-4 (IL-4) (Genzyme, Boston, Ma.). On Day 13 of culture, an aliquot from each line was tested for reactivity to MBP. Lines reactive to MBP were then tested for reactivity to overlapping oligopeptide 20-mers encompassing the human MBP sequence as shown in Table 1 above. For MHC restriction experiments, lines reactive to an MBP peptide were restimulated for two more cycles, first with MBP and then with the specific MBP fragment recognized by that line. In a subgroup of patients, the frequency of T-cells recognizing proteolipid protein (PLP), another major encephalitogenic central nervous system antigen, was investigated.

MBP and PLP frequency analysis was performed on patients with definite, relapsing-remitting MS (as diagnosed by Magnetic Resonance Imaging—"MRI"—and clinical examination), as well as on subjects with other neurologic diseases and normal subjects (all age and sex matched to the MS patients).

The results are shown in Table 3A below.

Patients with MS were Caucasian and had well-characterized relapsing remitting disease with at least two exacerbations within the previous 24 months and positive lesions on Magnetic Resonance Imaging (MRI) at the time of blood drawing. Subjects with other central nervous system diseases had the following diagnoses: 1–3 weeks after either cerebrovascular accident [4] or brain trauma with CNS hemorrhage [4]; metastatic brain tumor [2]. The total number of T-cell lines reactive with either MBP or PLP and the total number of T-cell lines generated are shown in Table 3A ("Ag" means "antigen"). In addition, the frequencies of MBP- and PLP-reactive lines were calculated separately for each subject by dividing the number of MBP-reactive lines by the total number of lines generated and the mean value ± SEM are given.

While the frequency of MBP reactive lines was slightly higher in subjects with MS as compared to the other subjects, this was not statistically significant. There was more reactivity to PLP in patients with MS as compared to subjects with other neurologic diseases, but this did also not reach statistical significance.

Of a total of 302 cell lines from patients with MS that could be expanded and confirmed to react with MBP on repeated analysis, 140 (46.4%) reacted with MBP residues 84–102. In the control groups, 11 of a total of 100 MBP reactive T-cell lines (11.0%) recognized this MBP peptide. The actual frequency of T-cells derived from the peripheral blood that reacted with each MBP peptide for each individual subject was calculated. The mean values for patients with MS and the control subjects are shown in the next-to-rightmost column of Table 3A.

50,000 T-line cells were plated in triplicate with 50,000 irradiated APC, MNC (mononuclear cells) (Hafler, D. A., et al., *J. Exp. Med.* 167: 1313, 1988) for 72 hours in round bottom 96-well microtiter plates and wells were pulsed with [$^3$H]-thymidine for the last 18 hours of culture. APC MNC were either cultured alone, pulsed with 100 micrograms/ml of synthetic MBP peptide 84–102, (determined to be the optimal concentration of peptide to induce proliferation), or pulsed with 100 micrograms/ml of MBP. The average counts per minute (CPM) values for triplicate wells are shown in Table 4. DR and DQw haplotypes are given and haplotypes common with the patient (top line), who was positive for DR2, DR7, DQw1, DQw3, are underlined.

Proliferation of T-cell lines using a panel of different mononuclear cells (MNC) as antigen presenting cells (APC) are shown. Five T-cell lines reactive to MBP amino acid residues 84–102 from subject Hy were expanded by repeated cycles of stimulation with autologous irradiated MNC, pulsed with synthetic MBP peptide 84–102 and examined for recognition of this region of MBP.

For these studies, the panel of five T cell lines reactive with MPB residues 84–102 were plated with autoautologous APC MNC, as above, in the presence of monoclonal antibodies (mAbs) (final concentration of 1:100) recognizing different MHC Class II gene products. (The nomenclature

TABLE 3A

| | | SEX (%) | MHC (%) | | | | #Ag REACTIVE LINES/ TOTAL # LINES | | MEAN FREQUENCY OF Ag REACTIVE LINES (%) | |
|---|---|---|---|---|---|---|---|---|---|---|
| | AGE | (M/F) | DR2 | DR4 | DRw11 | DQw1 | MBP | PLP | MBP | PLP |
| MULTIPLE SCLEROSIS (n = 23) | 34.2 + 1.4 | 35/65 | 60.9 | 26.1 | 13.0 | 78.2 | 554/7746 | 20/432 | 7.18 ± 2.38 | 3.34 ± 1.56 |
| OTHER NEUROLOGIC DISEASE (n = 10) | 38.7 + 3.2 | 43/57 | 14.3 | 0.0 | 42.9 | 85.7 | 118/2880 | 3/384 | 4.10 ± 1.04 | 0.90 ± 0.62 |
| NORMAL (n = 6) | 30.3 + 1.5 | 50/50 | 16.7 | 0.0 | 50.0 | 66.6 | 73/1742 | ND | 4.70 ± 1.58 | ND |
| DR2 + CONTROLS (n = 6) | 32.0 + 2.9 | 50/50 | 100 | 16.7 | 0.0 | 100 | 53/1728 | ND | 3.08 ± 2.06 | ND | used for the antobodies is from the Tenth International Histocompatibility Workshop; their specificity is also given). The results are set forth in Table 4 below.

The MHC association with residues of the T-cell lines reactive with an immunodominant MBP epitope was determined. The results are set forth in Table 5 below. More

TABLE 4

| | | T cell lines from patient Hy | | | | | | | | | | | | | | |
|---|---|---|---|---|---|---|---|---|---|---|---|---|---|---|---|---|
| MHC | Phenotype | 1A8 | | | 2C9 | | | 2E11 | | | 2H9 | | | 3A10 | | |
| of DR | APC DQw | APC | MBP | peptide 84-102 | APC | MBP | peptide 84-102 | APC | MBP | peptide 84-102 | APC | MBP | peptide 84-102 | APC | MBP | peptide 84-102 |
| 2.7 | 1.3 | 32 | 21,192 | 10,747 | 83 | 3,263 | 14,991 | 148 | 18,593 | 30,368 | 169 | 2,797 | 10,444 | 139 | 6,887 | 24,411 |
| 2 | 1 | 83 | 56 | 32 | 82 | 78 | 112 | 217 | 52,939 | 49,399 | 636 | 327 | 658 | 23 | 28 | 26 |
| 4.7 | 2.3 | 32 | 26 | 53 | 45 | 55 | 142 | 37 | 167 | 81 | 226 | 258 | 263 | 306 | 719 | 915 |
| 3 | 2 | 46 | 32 | 52 | 43 | 44 | 110 | 101 | 98 | 349 | 769 | 402 | 1,973 | 23 | 31 | 100 |
| 3.10 | 1.2 | 35 | 30,737 | 49,144 | 158 | 25 | 80 | 36 | 58 | 42 | 49 | 54 | 46 | 42 | 22,823 | 31,121 |
| 2.7 | 1.2 | 38 | 40 | 47 | 43 | 39 | 43 | 78 | 53,441 | 32,357 | 261 | 190 | 289 | 33 | 19 | 36 |
| 7.w11 | 2.7 | 44 | 39 | 54 | 57 | 124 | 259 | 34 | 25 | 33 | 51 | 58 | 97 | 967 | 1,214 | 2,744 |

Figure 3:
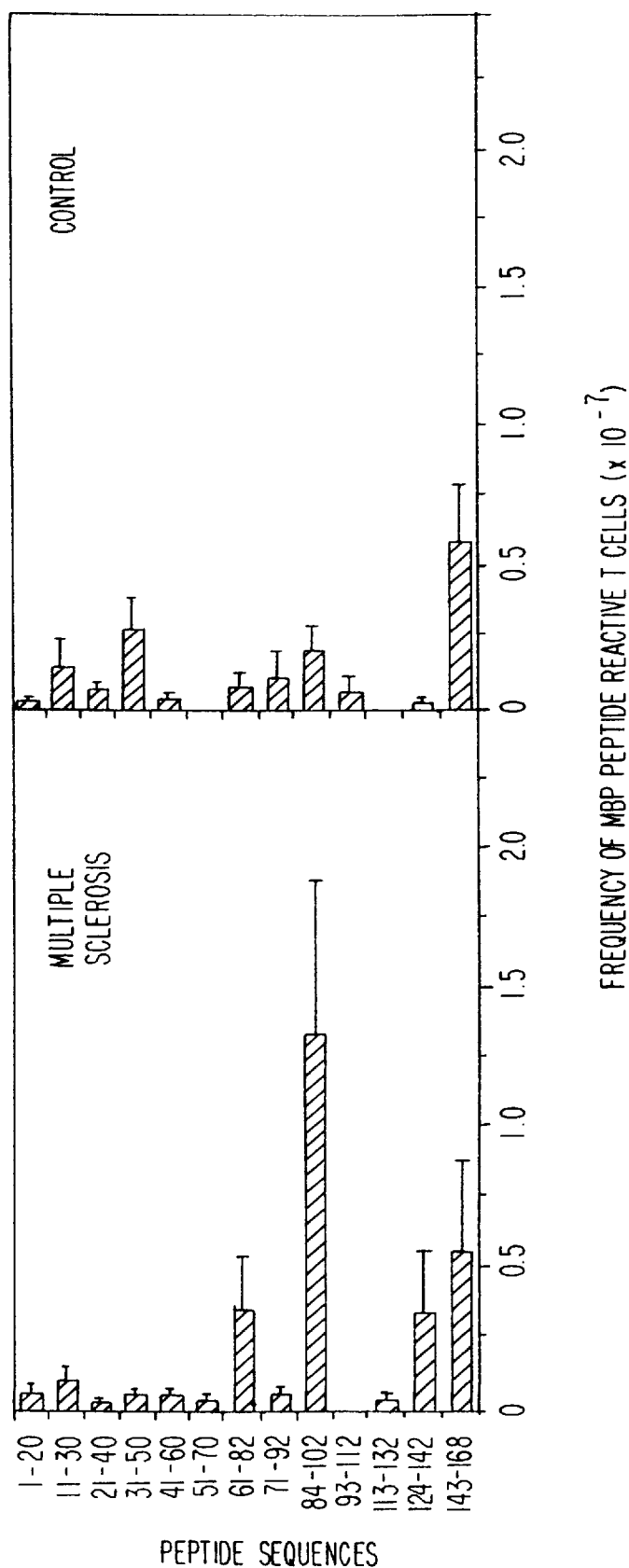
FIG. 3 is a bar graph showing the frequency of MBP reactive T-cells to different human MBP peptides isolated from MS patients and controls.
Figure 4A:
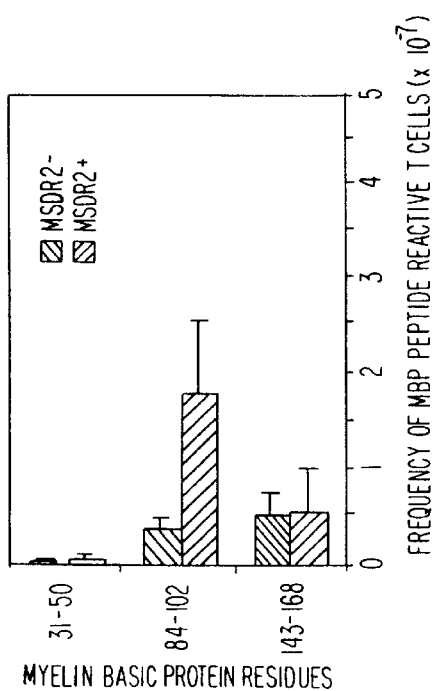
FIG. 4 is a series of bar graphs showing the reactivity of T-cells isolated from MS patients and controls to different regions of the human MBP polypeptide in relationship to whether these patients have certain MHC antigens.
Figure 4B:
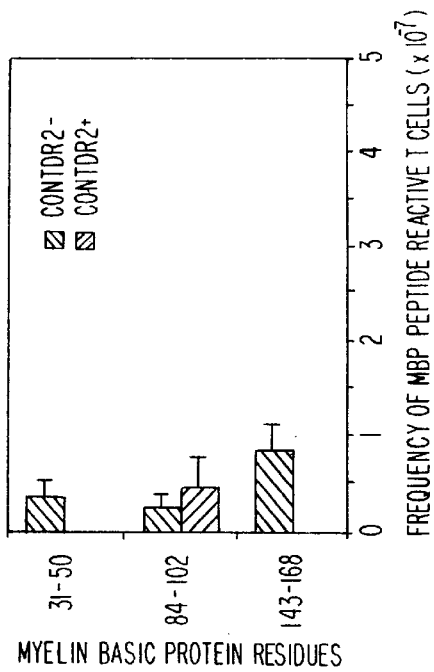
Figure 4C:
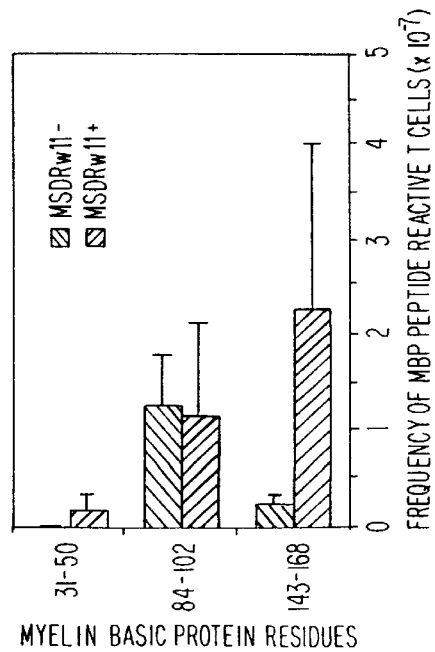
Figure 4D:
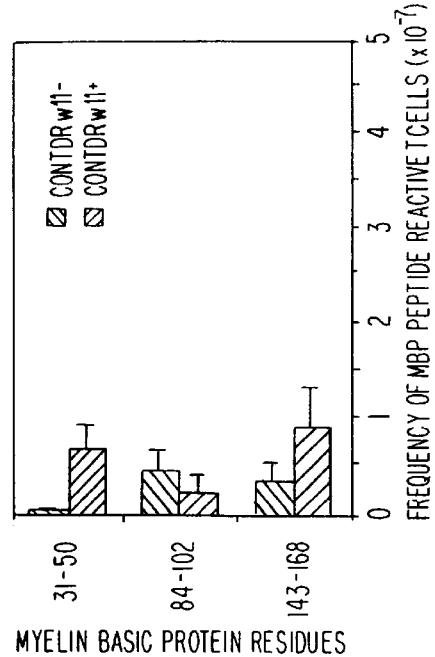

The frequency of peptide specific cell lines from normal subjects and other neurologic disease controls were virtually identical and thus combined for analysis. The mean frequency of T-cell lines from subjects with MS that were selectively reactive to MBP residues 84–102 [SEQ ID NO: 1] was higher as compared with controls (FIG. 3). Significant but less striking increases in reactivity to MBP residues 61–82 [SEQ ID NO: 20] and 124–142 [SEQ ID NO: 24] were also observed in MS patients, while both MS and control subjects showed high frequencies of T-cell lines reactive with MBP residues 143–168 [SEQ ID NO: 25]. The DR2, DQw1 haplotype was very infrequent in the control subjects and more common in patients with MS (Table 4). An association was observed between the DR2 phenotype and both the proportion or the frequency of T-cell lines reactive to MBP residues 84–102 [SEQ ID NO: 1] (FIG. 4).

To determine if T-cell reactivity to MBP residues 84–102 was associated with DR2, DQw1 expression in non-MS subjects, an additional 6 normal subjects with DR2, DQw1 phenotype were investigated. The results are shown in FIG. 4.

A DR2 association was also observed among controls in terms of the proportion of T-cell lines reactive with MBP residues 84–102 (DR2+ controls, 31.0±10–0.8%; DR2−, 10.1±0.4%), though the total frequency of lines reactive with this region of MBP was less than that in patients with MS (FIG. 4). Though DQw1 is in linkage dissociation with DR2 as well as with DR1 and DRw10, independent analysis of peptide reactivity revealed no association with DQw1 phenotype expression.

The DRw11 phenotype was more common in controls than in subjects with MS (Table 3A). DRw11 was positively associated with the frequency of lines reactive to MBP residues 142–168 in patients with MS and controls, but not with the frequency of lines reactive with MBP residues 84–102 [SEQ ID NO: 1] (FIG. 2). Reactivity to MBP residues 31–50 [SEQ ID NO: 17], which was predominantly observed in control subjects, was associated with DRw11. Other MHC associations were not observed.

specifically, it was determined whether the MHC haplotypes were used to present antigen in the T-cell lines reactive with an immunodominant MBP epitope.

TABLE 5

| | T-cell lines from patient Hy | | | | | |
|---|---|---|---|---|---|---|
| | | 1A8 | 2C9 | 2E11 | 2H9 | 3A10 |
| | APC alone | 32 | 83 | 39 | 50 | 139 |
| | no mAb | 10,747 | 14,991 | 3,325 | 8,659 | 24,411 |
| mAb specificity | control mAb | 11,375 | 15,322 | 4,131 | 8,156 | 27,363 |
| anti-DR | PL8 | 11,051 | 41 | 31 | 142 | 25,016 |
| | L.243 | 16,792 | 586 | 22 | 36 | 21,148 |
| | 65P4.1 | 19,119 | 405 | 46 | 92 | 26,412 |
| anti-DQ | 1A3 | 4,851 | 11,444 | 2,102 | 5,446 | 15,714 |
| | Tu22 | 1,189 | 13,442 | 1,073 | 7,661 | 13,488 |
| | Leu10 | 1,128 | 14,924 | 2,255 | 7,678 | 13,090 |
| anti-DP | B7121 | 7,917 | 15,922 | 2,337 | 6,689 | 23,452 |
| anti-DR + DP | Tu35 | 13,606 | 75 | 21 | 42 | 27,104 |

Monoclonal antibody blocking studies of five T-cell lines reactive with MBP residues 84–102 suggested that both DR and DQ molecules could function as restricting elements. Among clones blocked by anti-DR mAb, clone 2E11 proliferated in response to MBP residues 84–102 with the panel of DR2+ APC while 2C9 and 2H9 proliferated only with autologous APC (Table 5). The recognition of peptide by clones 1A8 and 3A10, which were partially blocked by anti-DQ mAbs was restricted to APC from the responder and one of two APC donor subjects expressing DQw1.

To investigate further the relationship between MHC expression and frequency of T-cell reactivity to immunodominant MBP epitopes, a family with one afflicted sibling expressing both DR2 and DRw11 phenotypes was studied.

The family members of an MS patient expressing the DR2, DQw1; DRw11, DRw52, DQw1 Class II MHC haplotypes were examined for the frequency of T-cell lines reactive with MBP residues 84–102 and 143–168.

A total of 1,728 individual T-cell lines were generated from both parents and 4 siblings and the number of lines reactive with either MBP peptide 84–102 or 143–168 were determined.

$2 \times 10^5$ MNC in each of 288 wells (three 96 well round bottom plates) were cultured with MBP (10 micrograms/ml) as outlined above for each subject. On day 16, each T-cell line was analyzed for reactivity to synthetic peptides corresponding to the MBP residues 84–102 and 143–168. The number of lines reactive with each peptide (stimulation index SI>3, delta CPM>500) generated per subject are shown. The actual stimulation indices were generally >20. P1 and P2=parents; S1–S3=siblings. The results are set forth in Table 6 below.

TABLE 6

| PATIENT | P1 | P2 | S1 | S2 | S3 |
|---|---|---|---|---|---|
| DR2 | DR4 DRw53 | DR2 | DR4 DRw53 | DR4 DRw53 | DR2 |
| DQw1 | DQw3 | DQw1 | DQw3 | DQw3 | DQw1 |
| DRw11 | DRw11 | DRw6 | DRw6 | DRw6 | DRw4 |
| DRw52 | DRw52 | DRw52 | DRw52 | DRw52 | DRw53 |
| DQw1 | DQw1 | DQw1 | DQw1 | DQw1 | DQw3 |
| MBP peptide | | | | | |
| 84-102 | 49 | 1 | 4 | 6 | 1 | 7 |
| 143-168 | 41 | 14 | 0 | 3 | 2 | 2 |

The DR2+, DRw11+ patient had a high frequency of T-cell lines reactive to both MBP residues 84–102 and 143–168. The DRw11+ parent preferentially recognized MBP residues 143–168, while the DR2+ parent preferentially recognized MBP residues 84–102. The frequency of MBP peptide reactive lines, however, was lower than that of the patient. One sibling was DR2+ and preferentially recognized MBP residues 84–102. Of two HLA identical siblings with DR4, DQw3/DRw6, DQw1, one reacted to MBP peptide 84–102 whereas the other did not. Although DQw1 may restrict recognition of MBP residues 84–102, other factors such as inherited TCR polymorphism may have influenced T-cell reactivity to the MBP autoantigen in one of the DR4, DQw3/DRw6, DQw1 siblings. This family linkage analysis suggested that optimum recognition of immunodominant MBP epitopes requires specific Class II MHC alleles both in patients with MS and in controls. In total, these studies indicate that although control subjects expressing DR2 appear to preferentially recognize the same MBP determinant as compared to DR2+ MS patients, their frequency in the blood is less than that of patients with MS.

EXAMPLE 4
Sequence of VB17 TCR

The T-cell receptor VB17+ PCR products from six cloned T-cell lines were sequenced by the dideoxy method as described reactive with MBP residues 84–102 (Patients Hy, Fr and Ns) in Example 1. The DNAs were amplified using PCR primers for the VB17-leader sequence and the TCR CB region described above in Example 1. The amplified DNA was cloned into M13 and sequenced using the well-known dideoxy method (3 M13 plaques per T-cell line). The results are set forth in Table 7 below.

The nucleotide sequences listed in Table 7 above are identified as follows: Hy.1A8 VB, DB and JB are identified as [SEQ ID NO: 49], [SEQ ID NO: 50] and [SEQ ID NO: 51], Hy.2C9 VB, DB and JB are identified as [SEQ ID NO: 52], [SEQ ID NO: 53] and [SEQ ID NO: 54], respectively; Hy.3A10 VB, DB and JB are identified as [SEQ ID NO: 55], [SEQ ID NO: 56] and [SEQ ID NO: 57], respectively; Hy.2C8 VB, DB and JB are identified as [SEQ ID NO: 58], [SEQ ID NO: 59] and [SEQ ID NO: 60], respectively; Fn.1G6 VB, DB and JB are identified as [SEQ ID NO: 61], [SEQ ID NO: 62] and [SEQ ID NO: 63], respectively; and Ns.1G11 VB, DB and JB are identified as [SEQ ID NO: 64], [SEQ ID NO: 65] and [SEQ ID NO: 66], respectively.

The peptides listed in Table 7 above are identified as follows: Hy.1A8 VB, DB and JB are identified as [SEQ ID NO: 67], [SEQ ID NO: 68] and [SEQ ID NO: 69], Hy.2C9 VB, DB and JB are identified as [SEQ ID NO: 70], [SEQ ID NO: 71] and [SEQ ID NO: 72], respectively; Hy.3A10 VB, DB and JB are identified as [SEQ ID NO: 73], [SEQ ID NO: 74] and [SEQ ID NO: 75], respectively; Hy.2C8 VB, DB and JB are identified as [SEQ ID NO: 76], [SEQ ID NO: 77] and [SEQ ID NO: 78], respectively; Fn.1G6 VB, DB and JB are identified as [SEQ ID NO: 79], [SEQ ID NO: 80] and [SEQ ID NO: 81], respectively; and Ns.1G11 VB, DB and JB are identified as [SEQ ID NO: 82], [SEQ ID NO: 83] and [SEQ ID NO: 84], respectively.

It should be noted above that the VB17 sequence of all 4 T-cell lines established from MS patient Hy were 100% homologous to the published VB17 sequence.

The following is a concordance between the 3-letter and the 1-letter codes for aminoacids. It is provided for convenience.

Aspartic acid (Asp, D)
Glutamic acid (Glu, E)
Lysine (Lys, K)
Arginine (Arg, R)
Histidine (His, H)
Tyrosine (Tyr, Y)
Cysteine (Cys, C)
Asparagine (Asn, N)
Glutamine (Gln, Q)
Serine (Ser, S)
Threonine (Thr, T)
Glycine (Gly, G)
Alanine (Ala, A)
Valine (Val, V)
Leucine (Leu, L)
Isoleucine (Ile, I)
Methionine (Met, M)
Proline (Pro, P)
Phenylalanine (Phe, F)
Tryptophan (Trp, W)

TABLE 7

| | VB | DB | JB | |
|---|---|---|---|---|
| Hy.1A8 | TyrLeuCysAlaSerSer TATCTCTGTRGCCAGTAGT | ThrAspTrpSer ACTGACTGGAGC | SerTyrAsnGluGlnPhe TCCTACAATGAGCAGTTC | VB17-JB2.1 |
| Hy.2C9 | TyrLeuCysAlaSerSer TATCTCTGTGCCAGTAGT | ThrAspTrpSer ACTGACTGGAGC | SerTyrAsnGluGlnPhe TCCTACAATGAGCAGTTC | VB17-JB2.1 |
| Hy.3A10 | TyrLeuCysAlaSerSer TATCTCTGTGCCAGTAGT | ThrAspTrpSer ACTGACTGGAGC | SerTyrAspGluGlnPhe TCCTACAATGAGCAGTTC | VB17-JB2.1 |
| Hy.2C8 | TyrLeuCysAlaSerArg TATCTCTGTGCCAGTAGG | ThrSerGly ACTAGCCGGC | SerTyrAsnGluGlnPhe TCCTACAACGAGCAGTTC | VB17-JB2.1 |
| Fn.1G6 | TyrLeuCysAlaSerSer TATCTCTGTGCCAGTAGT | IleProPro ATCCCTCCA | SerTyrGluGlnTyrPhe TCCTACGAGCAGTACTTC | VB17-JB2.7 |
| Ns.1G11 | TyrLeuCysAlaSerSer TATCTETGTGCCAGTAGT | AlaAspArg GEGGACAGG | AspGlnProGlnHisPhe GATCAGCCCCAGCATTTT | VB17-JB1.5 |

What is claimed:

1. A peptide the amino acid sequence of which is all or a segment of the sequence SEQ ID NO: 2 provided that said segment comprises a portion of the sequence SEQ ID NO: 1 sufficient to impart to said peptide the property of stimulating, as determined by proliferation assay, the subgroup of T-cells of the DR2+ type from remitting-relapsing multiple sclerosis patients that is reactive with another peptide the sequence of which consists of SEQ ID NO: 1, said peptide stimulating said subgroup of T-cells to about the same degree as said another peptide.

2. The peptide of claim 1 the sequence of which consists of the sequence SEQ ID NO: 1.

3. The peptide of claim 1 the sequence of which comprises at least the sequence SEQ ID NO: 1.

* * * * *

UNITED STATES PATENT AND TRADEMARK OFFICE
CERTIFICATE OF CORRECTION

PATENT NO.        : 6,039,947                                               Page 1 of 1
APPLICATION NO. : 08/297395
DATED             : March 21, 2000
INVENTOR(S)       : Howard L. Weiner et al.

It is certified that error appears in the above-identified patent and that said Letters Patent is hereby corrected as shown below:

Column 6, lines 10-11, after "comprising the sequence" delete "JYYSQIVNDFQKGDIAEGYS" and substitute -- YYSQIVNDFQKGDIAEGYS --.

Signed and Sealed this

Third Day of October, 2006

JON W. DUDAS
*Director of the United States Patent and Trademark Office*

SEQUENCE LISTING

<160> NUMBER OF SEQ ID NOS: 84

<210> SEQ ID NO 1
<211> LENGTH: 19
<212> TYPE: PRT
<213> ORGANISM: Homo sapiens

<400> SEQUENCE: 1

Asp Glu Asn Pro Val Val His Phe Phe Lys Asn Ile Val Thr Pro Arg
1               5                   10                  15

Thr Pro Pro

<210> SEQ ID NO 2
<211> LENGTH: 40
<212> TYPE: PRT
<213> ORGANISM: Homo sapiens

<400> SEQUENCE: 2

Ser Leu Pro Gln Lys Ser His Gly Arg Thr Gln Asp Glu Asn Pro Val
1               5                   10                  15

Val His Phe Phe Lys Asn Ile Val Thr Pro Arg Thr Pro Pro Pro Ser
            20                  25                  30

Gln Gly Lys Gly Arg Gly Leu Ser
        35                  40

<210> SEQ ID NO 3
<211> LENGTH: 6
<212> TYPE: PRT
<213> ORGANISM: Artificial Sequence
<220> FEATURE:
<223> OTHER INFORMATION: VB8.2 peptide sequence

<400> SEQUENCE: 3

Thr Leu Cys Ala Ser Ser
1               5

<210> SEQ ID NO 4
<211> LENGTH: 6
<212> TYPE: PRT
<213> ORGANISM: Artificial Sequence
<220> FEATURE:
<223> OTHER INFORMATION: VB8.2 peptide sequence

<400> SEQUENCE: 4

Thr Leu Cys Ala Ser Arg
1               5

<210> SEQ ID NO 5
<211> LENGTH: 10
<212> TYPE: PRT
<213> ORGANISM: Homo sapiens
<220> FEATURE:

<400> SEQUENCE: 5

Asp Thr Asp Lys Gly Glu Val Tyr Asp Gly
1               5                   10

<210> SEQ ID NO 6
<211> LENGTH: 10
<212> TYPE: PRT
<213> ORGANISM: Homo sapiens
<220> FEATURE:

```
<400> SEQUENCE: 6

Phe Gln Lys Gly Asp Ile Ala Glu Gly Tyr
1               5                   10

<210> SEQ ID NO 7
<211> LENGTH: 19
<212> TYPE: PRT
<213> ORGANISM: Homo sapiens

<400> SEQUENCE: 7

Tyr Tyr Ser Gln Ile Val Asn Asp Phe Gln Lys Gly Asp Ile Ala Glu
1               5                   10                  15

Gly Tyr Ser

<210> SEQ ID NO 8
<211> LENGTH: 71
<212> TYPE: PRT
<213> ORGANISM: Homo sapiens

<400> SEQUENCE: 8

Leu Arg Cys His Gln Thr Glu Asn His Arg Tyr Met Tyr Arg Gln Asp
1               5                   10                  15

Pro Gly His Gly Leu Arg Leu Ile His Tyr Ser Tyr Gly Val Lys Asp
            20                  25                  30

Thr Asp Lys Gly Glu Val Ser Asp Gly Thr Ser Val Ser Arg Ser Lys
        35                  40                  45

Thr Glu Asp Phe Leu Leu Thr Leu Glu Ser Ala Thr Ser Ser Gln Thr
    50                  55                  60

Ser Val Tyr Phe Cys Ala Asn
65                  70

<210> SEQ ID NO 9
<211> LENGTH: 213
<212> TYPE: DNA
<213> ORGANISM: Homo sapiens

<400> SEQUENCE: 9
ctgagatgtc accagactga gaaccaccgc tatatgtacc gacaagaccc ggggcatggg     60
ctgaggctga tccattactc atatggtgtt aaagatactg acaaggaga agtctcagat    120 ggctatagtg tctctagatc aaagacagag gatttcctcc tcactctgga gtccgctacc    180
agctcccaga catctgtgta cttctgtgcc aat                                213

<210> SEQ ID NO 10
<211> LENGTH: 94
<212> TYPE: PRT
<213> ORGANISM: Homo sapiens

<400> SEQUENCE: 10

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Thr
    50                  55                  60

Ser Val Ser Arg Glu Lys Lys Glu Ser Phe Pro Leu Thr Val Thr Ser
65                  70                  75                  80
```

```
Ala Gln Lys Asn Pro Thr Ala Phe Tyr Leu Cys Ala Ser Ser
                85                  90
```

<210> SEQ ID NO 11
<211> LENGTH: 282
<212> TYPE: DNA
<213> ORGANISM: Homo sapiens

<400> SEQUENCE: 11

```
gatggtggaa tcactcagtc cccaaagtac ctgttcagaa aggaaggaca gaatgtgacc      60
ctgagttgtg aacagaattt gaaccacgat gccatgtact ggtaccgaca ggacccaggg     120
caagggctga gattgatcta ctactcacag atagtaaatg actttcagaa aggagatata     180
gctgaagggt acagcgtctc tcgggagaag aaggaatcct ttcctctcac tgtgacatcg     240
gcccaaaaga acccgacagc tttctatctc tgtgccagta gt                        282
```

<210> SEQ ID NO 12
<211> LENGTH: 30
<212> TYPE: DNA
<213> ORGANISM: Homo sapiens

<400> SEQUENCE: 12

```
gatactgaca aaggagaagt ctcagatggc                                       30
```

<210> SEQ ID NO 13
<211> LENGTH: 30
<212> TYPE: DNA
<213> ORGANISM: Homo sapiens

<400> SEQUENCE: 13

```
tttcagaaag gagatatagc tgaagggtac                                       30
```

<210> SEQ ID NO 14
<211> LENGTH: 20
<212> TYPE: PRT
<213> ORGANISM: Homo sapiens

<400> SEQUENCE: 14

```
Ala Ser Gln Lys Arg Pro Ser Gln Arg His Gly Ser Lys Tyr Leu Ala
 1               5                  10                  15

Thr Ala Ser Thr
            20
```

<210> SEQ ID NO 15
<211> LENGTH: 20
<212> TYPE: PRT
<213> ORGANISM: Homo sapiens

<400> SEQUENCE: 15

```
Gly Ser Lys Tyr Leu Ala Thr Ala Ser Thr Met Asp His Ala Arg His
 1               5                  10                  15

Gly Phe Leu Pro
            20
```

<210> SEQ ID NO 16
<211> LENGTH: 20
<212> TYPE: PRT
<213> ORGANISM: Homo sapiens

<400> SEQUENCE: 16

```
Met Asp His Ala Arg His Gly Phe Leu Pro Arg His Arg Asp Thr Gly
```

```
                1               5              10              15

Ile Leu Asp Ser
                20

<210> SEQ ID NO 17
<211> LENGTH: 20
<212> TYPE: PRT
<213> ORGANISM: Homo sapiens

<400> SEQUENCE: 17

Arg His Arg Asp Thr Gly Ile Leu Asp Ser Ile Gly Arg Phe Phe Gly
1               5              10              15

Gly Asp Arg Gly
                20

<210> SEQ ID NO 18
<211> LENGTH: 20
<212> TYPE: PRT
<213> ORGANISM: Homo sapiens

<400> SEQUENCE: 18

Ile Gly Arg Phe Phe Gly Gly Asp Arg Gly Ala Pro Lys Arg Gly Ser
1               5              10              15

Gly Lys Asp Ser
                20

<210> SEQ ID NO 19
<211> LENGTH: 20
<212> TYPE: PRT
<213> ORGANISM: Homo sapiens

<400> SEQUENCE: 19

Ala Pro Lys Arg Gly Ser Gly Lys Asp Ser His His Pro Ala Arg Thr
1               5              10              15

Ala His Tyr Gly
                20

<210> SEQ ID NO 20
<211> LENGTH: 20
<212> TYPE: PRT
<213> ORGANISM: Homo sapiens

<400> SEQUENCE: 20

His His Pro Ala Arg Thr Ala His Tyr Gly Ser Leu Pro Gln Lys Ser
1               5              10              15

His Gly Arg Thr
                20

<210> SEQ ID NO 21
<211> LENGTH: 20
<212> TYPE: PRT
<213> ORGANISM: Homo sapiens

<400> SEQUENCE: 21

Ser Leu Pro Gln Lys Ser His Gly Arg Thr Gln Asp Glu Asn Pro Val
1               5              10              15

Val His Phe Phe
                20

<210> SEQ ID NO 22
<211> LENGTH: 20
<212> TYPE: PRT
```

<213> ORGANISM: Homo sapiens

<400> SEQUENCE: 22

Lys Asn Ile Val Thr Pro Arg Thr Pro Pro Ser Gln Gly Lys Gly
 1               5                  10                  15

Arg Gly Leu Ser
             20

<210> SEQ ID NO 23
<211> LENGTH: 20
<212> TYPE: PRT
<213> ORGANISM: Homo sapiens

<400> SEQUENCE: 23

Leu Ser Arg Phe Ser Trp Gly Ala Glu Gly Gln Arg Pro Gly Phe Gly
 1               5                  10                  15

Tyr Gly Gly Arg
             20

<210> SEQ ID NO 24
<211> LENGTH: 19
<212> TYPE: PRT
<213> ORGANISM: Homo sapiens

<400> SEQUENCE: 24

Arg Pro Gly Phe Gly Tyr Gly Gly Arg Ala Ser Asp Tyr Lys Ser Ala
 1               5                  10                  15

His Lys Gly

<210> SEQ ID NO 25
<211> LENGTH: 20
<212> TYPE: PRT
<213> ORGANISM: Homo sapiens

<400> SEQUENCE: 25

Phe Lys Gly Val Asp Ala Gln Gly Thr Leu Ser Lys Ile Phe Lys Leu
 1               5                  10                  15

Gly Gly Arg Asp
             20

<210> SEQ ID NO 26
<211> LENGTH: 30
<212> TYPE: DNA
<213> ORGANISM: Homo sapiens

<400> SEQUENCE: 26
aagagagagc aaaaggaaac attcttgaac                                    30

<210> SEQ ID NO 27
<211> LENGTH: 30
<212> TYPE: DNA
<213> ORGANISM: Homo sapiens

<400> SEQUENCE: 27
gctccaaggc cacatacgag caaggcgtcg                                    30

<210> SEQ ID NO 28
<211> LENGTH: 30
<212> TYPE: DNA
<213> ORGANISM: Homo sapiens

<400> SEQUENCE: 28
aaaatgaaag aaaaaggaga tattcctgag                                        30

<210> SEQ ID NO 29
<211> LENGTH: 30
<212> TYPE: DNA
<213> ORGANISM: Homo sapiens

<400> SEQUENCE: 29
ctgaggccac atatgagagt ggatttgtca                                        30

<210> SEQ ID NO 30
<211> LENGTH: 30
<212> TYPE: DNA
<213> ORGANISM: Homo sapiens

<400> SEQUENCE: 30
cagagaaaca aaggaaactt ccctggtcga                                        30

<210> SEQ ID NO 31
<211> LENGTH: 30
<212> TYPE: DNA
<213> ORGANISM: Homo sapiens

<400> SEQUENCE: 31
gggtgcggca gatgactcag ggctgcccaa                                        30

<210> SEQ ID NO 32
<211> LENGTH: 30
<212> TYPE: DNA
<213> ORGANISM: Homo sapiens

<400> SEQUENCE: 32
ataaatgaaa gtgtgccaag tcgcttctca                                        30

<210> SEQ ID NO 33
<211> LENGTH: 30
<212> TYPE: DNA
<213> ORGANISM: Homo sapiens

<400> SEQUENCE: 33
aacgttccga tagatgattc agggatgccc                                        30

<210> SEQ ID NO 34
<211> LENGTH: 30
<212> TYPE: DNA
<213> ORGANISM: Homo sapiens

<400> SEQUENCE: 34
cattataaat gaaacagttc caaatcgctt                                        30

<210> SEQ ID NO 35
<211> LENGTH: 30
<212> TYPE: DNA
<213> ORGANISM: Homo sapiens

<400> SEQUENCE: 35
cttattcaga aagcagaaat aatcaatgag                                        30

<210> SEQ ID NO 36
<211> LENGTH: 30
<212> TYPE: DNA
<213> ORGANISM: Homo sapiens

<400> SEQUENCE: 36

-continued tccacagaga agggagatct ttcctctgag                    30

<210> SEQ ID NO 37
<211> LENGTH: 30
<212> TYPE: DNA
<213> ORGANISM: Homo sapiens

<400> SEQUENCE: 37
gatactgaca aaggagaagt ctcagatggc                    30

<210> SEQ ID NO 38
<211> LENGTH: 30
<212> TYPE: DNA
<213> ORGANISM: Homo sapiens

<400> SEQUENCE: 38
gtgactgata agggagatgt tcctgaaggg                    30

<210> SEQ ID NO 39
<211> LENGTH: 30
<212> TYPE: DNA
<213> ORGANISM: Homo sapiens

<400> SEQUENCE: 39
gatataaaca aaggagagat ctctgatgga                    30

<210> SEQ ID NO 40
<211> LENGTH: 30
<212> TYPE: DNA
<213> ORGANISM: Homo sapiens

<400> SEQUENCE: 40
catgataatc tttatcgacg tgttatggga                    30

<210> SEQ ID NO 41
<211> LENGTH: 30
<212> TYPE: DNA
<213> ORGANISM: Homo sapiens

<400> SEQUENCE: 41
tttcagaaag gagatatagc tgaagggtac                    30

<210> SEQ ID NO 42
<211> LENGTH: 30
<212> TYPE: DNA
<213> ORGANISM: Homo sapiens

<400> SEQUENCE: 42
gatgagtcag gaatgccaaa ggaacgattt                    30

<210> SEQ ID NO 43
<211> LENGTH: 30
<212> TYPE: DNA
<213> ORGANISM: Homo sapiens

<400> SEQUENCE: 43
caagaaacgg agatgcacaa gaagcgattc                    30

<210> SEQ ID NO 44
<211> LENGTH: 30
<212> TYPE: DNA
<213> ORGANISM: Homo sapiens -continued

```
<400> SEQUENCE: 44
accgacaggc tgcaggcagg ggcctccagc                                    30

<210> SEQ ID NO 45
<211> LENGTH: 29
<212> TYPE: DNA
<213> ORGANISM: Homo sapiens

<400> SEQUENCE: 45
ggcagacagg acccttgctg gtaggacac                                     29

<210> SEQ ID NO 46
<211> LENGTH: 30
<212> TYPE: DNA
<213> ORGANISM: Homo sapiens

<400> SEQUENCE: 46
ttctgatggc tcaaacacag cgacctcggg                                    30

<210> SEQ ID NO 47
<211> LENGTH: 30
<212> TYPE: DNA
<213> ORGANISM: Homo sapiens

<400> SEQUENCE: 47
agcaaccagg tgctctgcag tgtggtcctt                                    30

<210> SEQ ID NO 48
<211> LENGTH: 30
<212> TYPE: DNA
<213> ORGANISM: Homo sapiens

<400> SEQUENCE: 48
ccctggcccg aagaactgct cattgtagga                                    30

<210> SEQ ID NO 49
<211> LENGTH: 19
<212> TYPE: DNA
<213> ORGANISM: Homo sapiens

<400> SEQUENCE: 49
tatctctgtr gccagtagt                                                19

<210> SEQ ID NO 50
<211> LENGTH: 12
<212> TYPE: DNA
<213> ORGANISM: Homo sapiens

<400> SEQUENCE: 50
actgactgga gc                                                       12

<210> SEQ ID NO 51
<211> LENGTH: 18
<212> TYPE: DNA
<213> ORGANISM: Homo sapiens

<400> SEQUENCE: 51
tcctacaatg agcagttc                                                 18

<210> SEQ ID NO 52
<211> LENGTH: 18
<212> TYPE: DNA
<213> ORGANISM: Homo sapiens
```

```
<400> SEQUENCE: 52
tatctctgtg ccagtagt                                            18

<210> SEQ ID NO 53
<211> LENGTH: 12
<212> TYPE: DNA
<213> ORGANISM: Homo sapiens

<400> SEQUENCE: 53
actgactgga gc                                                  12

<210> SEQ ID NO 54
<211> LENGTH: 18
<212> TYPE: DNA
<213> ORGANISM: Homo sapiens

<400> SEQUENCE: 54
tcctacaatg agcagttc                                            18

<210> SEQ ID NO 55
<211> LENGTH: 18
<212> TYPE: DNA
<213> ORGANISM: Homo sapiens

<400> SEQUENCE: 55
tatctctgtg ccagtagt                                            18

<210> SEQ ID NO 56
<211> LENGTH: 12
<212> TYPE: DNA
<213> ORGANISM: Homo sapiens

<400> SEQUENCE: 56
actgactgga gc                                                  12

<210> SEQ ID NO 57
<211> LENGTH: 18
<212> TYPE: DNA
<213> ORGANISM: Homo sapiens

<400> SEQUENCE: 57
tcctacaatg agcagttc                                            18

<210> SEQ ID NO 58
<211> LENGTH: 18
<212> TYPE: DNA
<213> ORGANISM: Homo sapiens

<400> SEQUENCE: 58
tatctctgtg ccagtagg                                            18

<210> SEQ ID NO 59
<211> LENGTH: 10
<212> TYPE: DNA
<213> ORGANISM: Homo sapiens

<400> SEQUENCE: 59
actagccggc                                                     10

<210> SEQ ID NO 60
<211> LENGTH: 18
<212> TYPE: DNA
```

<213> ORGANISM: Homo sapiens

<400> SEQUENCE: 60
tcctacaacg agcagttc                                           18

<210> SEQ ID NO 61
<211> LENGTH: 18
<212> TYPE: DNA
<213> ORGANISM: Homo sapiens

<400> SEQUENCE: 61
tatctctgtg ccagtagt                                           18

<210> SEQ ID NO 62
<211> LENGTH: 9
<212> TYPE: DNA
<213> ORGANISM: Homo sapiens

<400> SEQUENCE: 62 atccctcca                                                      9

<210> SEQ ID NO 63
<211> LENGTH: 18
<212> TYPE: DNA
<213> ORGANISM: Homo sapiens

<400> SEQUENCE: 63
tcctacgagc agtacttc                                           18

<210> SEQ ID NO 64
<211> LENGTH: 18
<212> TYPE: DNA
<213> ORGANISM: Homo sapiens

<400> SEQUENCE: 64
tatctctgtg ccagtagt                                           18

<210> SEQ ID NO 65
<211> LENGTH: 9
<212> TYPE: DNA
<213> ORGANISM: Homo sapiens

<400> SEQUENCE: 65 gcggacagg                                                      9

<210> SEQ ID NO 66
<211> LENGTH: 18
<212> TYPE: DNA
<213> ORGANISM: Homo sapiens

<400> SEQUENCE: 66
gatcagcccc agcatttt                                           18

<210> SEQ ID NO 67
<211> LENGTH: 6
<212> TYPE: PRT
<213> ORGANISM: Homo sapiens

<400> SEQUENCE: 67

Tyr Leu Cys Ala Ser Ser
 1               5

<210> SEQ ID NO 68

```
<211> LENGTH: 4
<212> TYPE: PRT
<213> ORGANISM: Homo sapiens

<400> SEQUENCE: 68

Thr Asp Trp Ser
 1

<210> SEQ ID NO 69
<211> LENGTH: 6
<212> TYPE: PRT
<213> ORGANISM: Homo sapiens

<400> SEQUENCE: 69

Ser Tyr Asn Glu Gln Phe
 1               5

<210> SEQ ID NO 70
<211> LENGTH: 6
<212> TYPE: PRT
<213> ORGANISM: Homo sapiens

<400> SEQUENCE: 70

Tyr Leu Cys Ala Ser Ser
 1               5

<210> SEQ ID NO 71
<211> LENGTH: 4
<212> TYPE: PRT
<213> ORGANISM: Homo sapiens

<400> SEQUENCE: 71

Thr Asp Trp Ser
 1

<210> SEQ ID NO 72
<211> LENGTH: 6
<212> TYPE: PRT
<213> ORGANISM: Homo sapiens

<400> SEQUENCE: 72

Ser Tyr Asn Glu Gln Phe
 1               5

<210> SEQ ID NO 73
<211> LENGTH: 6
<212> TYPE: PRT
<213> ORGANISM: Homo sapiens

<400> SEQUENCE: 73

Tyr Leu Cys Ala Ser Ser
 1               5

<210> SEQ ID NO 74
<211> LENGTH: 4
<212> TYPE: PRT
<213> ORGANISM: Homo sapiens

<400> SEQUENCE: 74

Thr Asp Trp Ser
 1

<210> SEQ ID NO 75
<211> LENGTH: 6
<212> TYPE: PRT
```

```
<213> ORGANISM: Homo sapiens

<400> SEQUENCE: 75

Ser Tyr Asp Glu Gln Phe
 1               5

<210> SEQ ID NO 76
<211> LENGTH: 6
<212> TYPE: PRT
<213> ORGANISM: Homo sapiens

<400> SEQUENCE: 76

Tyr Leu Cys Ala Ser Arg
 1               5

<210> SEQ ID NO 77
<211> LENGTH: 3
<212> TYPE: PRT
<213> ORGANISM: Homo sapiens

<400> SEQUENCE: 77

Thr Ser Gly
 1

<210> SEQ ID NO 78
<211> LENGTH: 6
<212> TYPE: PRT
<213> ORGANISM: Homo sapiens

<400> SEQUENCE: 78

Ser Tyr Asn Glu Gln Phe
 1               5

<210> SEQ ID NO 79
<211> LENGTH: 6
<212> TYPE: PRT
<213> ORGANISM: Homo sapiens

<400> SEQUENCE: 79

Tyr Leu Cys Ala Ser Ser
 1               5

<210> SEQ ID NO 80
<211> LENGTH: 3
<212> TYPE: PRT
<213> ORGANISM: Homo sapiens

<400> SEQUENCE: 80

Ile Pro Pro
 1

<210> SEQ ID NO 81
<211> LENGTH: 6
<212> TYPE: PRT
<213> ORGANISM: Homo sapiens

<400> SEQUENCE: 81

Ser Tyr Glu Gln Tyr Phe
 1               5

<210> SEQ ID NO 82
<211> LENGTH: 6
<212> TYPE: PRT
<213> ORGANISM: Homo sapiens
```

```
<400> SEQUENCE: 82

Tyr Leu Cys Ala Ser Ser
1               5

<210> SEQ ID NO 83
<211> LENGTH: 3
<212> TYPE: PRT
<213> ORGANISM: Homo sapiens

<400> SEQUENCE: 83

Ala Asp Arg
1

<210> SEQ ID NO 84
<211> LENGTH: 6
<212> TYPE: PRT
<213> ORGANISM: Homo sapiens

<400> SEQUENCE: 84

Asp Gln Pro Gln His Phe
1               5
```